United States Patent [19]
Cheronis et al.

[11] Patent Number: 5,843,900
[45] Date of Patent: Dec. 1, 1998

[54] BRADYKININ ANTAGONISTS

[75] Inventors: John C. Cheronis, Lakewood; Albert Gyorkos, Westminster; Lyle W. Spruce, Arvada; Eric T. Whalley, Golden, all of Colo.

[73] Assignee: Cortech, Inc., Denver, Colo.

[21] Appl. No.: 465,672

[22] Filed: Jun. 5, 1995

Related U.S. Application Data

[63] Continuation-in-part of Ser. No. 296,185, Aug. 8, 1994, which is a continuation of Ser. No. 974,000, Nov. 10, 1992, abandoned, which is a continuation-in-part of Ser. No. 859,582, Mar. 27, 1992, abandoned, which is a continuation-in-part of Ser. No. 677,391, Apr. 1, 1991, abandoned.

[51] Int. Cl.$^6$ .............................. A61K 38/08; C07K 7/18
[52] U.S. Cl. ................................ 514/15; 514/2; 530/314; 530/328; 530/402; 530/408; 530/807; 530/816; 530/815
[58] Field of Search ............................. 514/15; 530/328, 530/402, 408, 807, 816, 815

[56] References Cited

U.S. PATENT DOCUMENTS

| | | |
|---|---|---|
| 4,618,598 | 10/1986 | Conn . |
| 4,894,443 | 1/1990 | Greenfield et al. . |
| 5,416,191 | 5/1995 | Cheronis et al. . |

FOREIGN PATENT DOCUMENTS

| | | |
|---|---|---|
| 0 370 453 A2 | 5/1990 | WIPO . |
| WO 89/01781 | 5/1990 | WIPO . |

OTHER PUBLICATIONS

Calixto, et al., "Nonpeptide Bradykinin Antagonists," pp. 97–129 (1991).

Carr, "The Effect of Anti–Inflammatory Drugs on Increased Vascular Permeability Induced by Chemical Mediators," *J. Pathology*, 108, 1–14 (1972).

Cheronis, et al. "Bradykinin Antagonists: Synthesis and In Vitro Activity of Bissuccinimidoalkane Peptide Dimers," In: *Recent Progress in Kinins*, pp. 551–558 (1992).

Kodama, H, et al., "Dimerization of Neurokinin A and B COOH–Terminal Heptapeptide Fragments Enhanced the Selectivity for Tachykinin Receptor Subtypes," *Euro. J. Pharmacol.*, 151, 317–320 (1988).

Stewart, J. M., et al., "Chemistry of Peptide B2 Bradykinin Antagonists," In: *Bradykinin Antagonists—Basic and Clinical Research.*, Burch, R. M. (ed.), Marcel Dekker, Inc., pp.51–96 (1991).

Stewart, J. M., et al., "Bradykinin Chemistry: Agonists and Antagonists," In. *Adv. Exp. Med. Biol.*, vol. 156, Fritz, H., (ed.), Plenum Press, New York, pp. 585–589 (1983).

Vavrek, R. J., et al., "Succinyl Bis–Bradykinins: Potent Agonists with Exceptional Resistance to Enzymatic Degradation," In: *Peptides—Structure and Function*, Hruby, V. J., et al., (eds.), Pierce Chemical Company, Rockford.

*Primary Examiner*—Cecilia J. Tsang
*Assistant Examiner*—Michael Borin
*Attorney, Agent, or Firm*—Cushman Darby & Cushman IP Group of Pillsbury Madison & Sutro LLP

[57] ABSTRACT

The present invention relates to pharmaceutically effective heterodimers comprising a bradykinin antagonist component covalently linked to a mu-opioid agonist component.

21 Claims, 9 Drawing Sheets

BRADYKININ ANTAGONISTS

This application is a continuation-in-part of U.S. Ser. No. 08/296,185 filed on Aug. 8, 1994, which is a continuation of U.S. Ser. No. 07/974,000 filed on Nov. 10, 1992, (abandoned) which is a continuation-in-part of U.S. Ser. No. 07/859,582 filed on Mar. 27, 1992, (abandoned) which is a continuation-in-part of U.S. Ser. No. 07/677,391 filed on Apr. 1, 1991, (abandoned) the contents of each which are incorporated herein in their entirety.

BACKGROUND OF THE INVENTION

This invention relates to compounds with combined bradykinin receptor antagonist and mu-opioid receptor agonist activities and to methods of using the same.

C-Fiber afferents are known to mediate both the sensation of pain as well as the neurogenic component of inflammation. These afferent neurons release a variety of neuropeptides in response to specific and non-specific stimuli in both the central nervous system (CNS) as well as in the peripherally innervated tissues. Some of these neuropeptides include: substance-P, neurokinin A, neurokinin B, calcitonin gene related peptide (CGRP), cholecystokinin (CCK), vasoactive intestinal polypeptide (VIP), and neuropeptide Y, among other neurotransmitters. To add to this complexity, different C-fibers appear to contain different amounts and/or ratios of these neuropeptides depending on the tissue innervated. All of these peptides have been shown to play contributory roles in the various neurogenic processes that have been implicated in numerous diseases and clinical syndromes.

One apparently common feature among this otherwise diverse group of neurons is that they all have mu-opioid receptors that modulate the release of these neuropeptides as well as afferent C-fiber activity. Both the endogenous enkephalins as well as other exogenously administered small molecular weight compounds such as morphine, oxymorphone, fentanyl and their derivatives will inhibit the release of the neuropeptides from peripheral C-fibers by acting as mu-opioid receptor agonists locally (at terminal mu-opioid receptors in the periphery) and in the CNS. This inhibition is independent of both the constellation of peptides contained in the specific C-fiber as well as the stimulus causing their release.

As a result, one important class of compounds considered to have a particularly good profile of activities for the treatment of conditions that are produced by combined humoral and neurogenic processes are bradykinin antagonist (BKAn)/mu-opioid receptor agonist heterodimers. These compounds would be expected to attenuate or block both the humoral component of the inflammatory process as represented by the kinins as well as the neurogenic aspects of inflammation produced by the release of the neuropeptides. In addition, one of the limiting aspects of the use of existing mu-opioid agonists is their propensity to produce sedation, confusion, and a depressed respiratory drive, not to mention their potential for the development of addiction and/or tolerance in the patients being treated with these agents. These undesirable aspects of mu-opioid receptor agonists are due to their ability to easily penetrate the CNS. BKAn/ mu-opioid receptor agonist heterodimers, however, should not penetrate the CNS due to the highly cationic nature of the BKAn.

Consequently, mu-opioid receptor agonist activity should be limited to the periphery and should result in a substantially reduced side effect/toxicity profile for these types of compounds.

SUMMARY OF THE INVENTION

The present invention provides heterodimeric compounds of the general formula (BKAn)(X)(Y) where BKAn is a bradykinin antagonist peptide; Y is a mu-opioid receptor agonist and X is a linking moiety. More specifically, the present invention provides heterodimeric compounds where the mu-opioid receptor agonist is selected from fentanyl, dihydromorphine and morphine or derivatives or analogs thereof. The present invention also provides heterodimers comprising improved linking moieties as well as improved bradykinin antagonists.

DETAILED DESCRIPTION OF THE INVENTION

Figure 1:
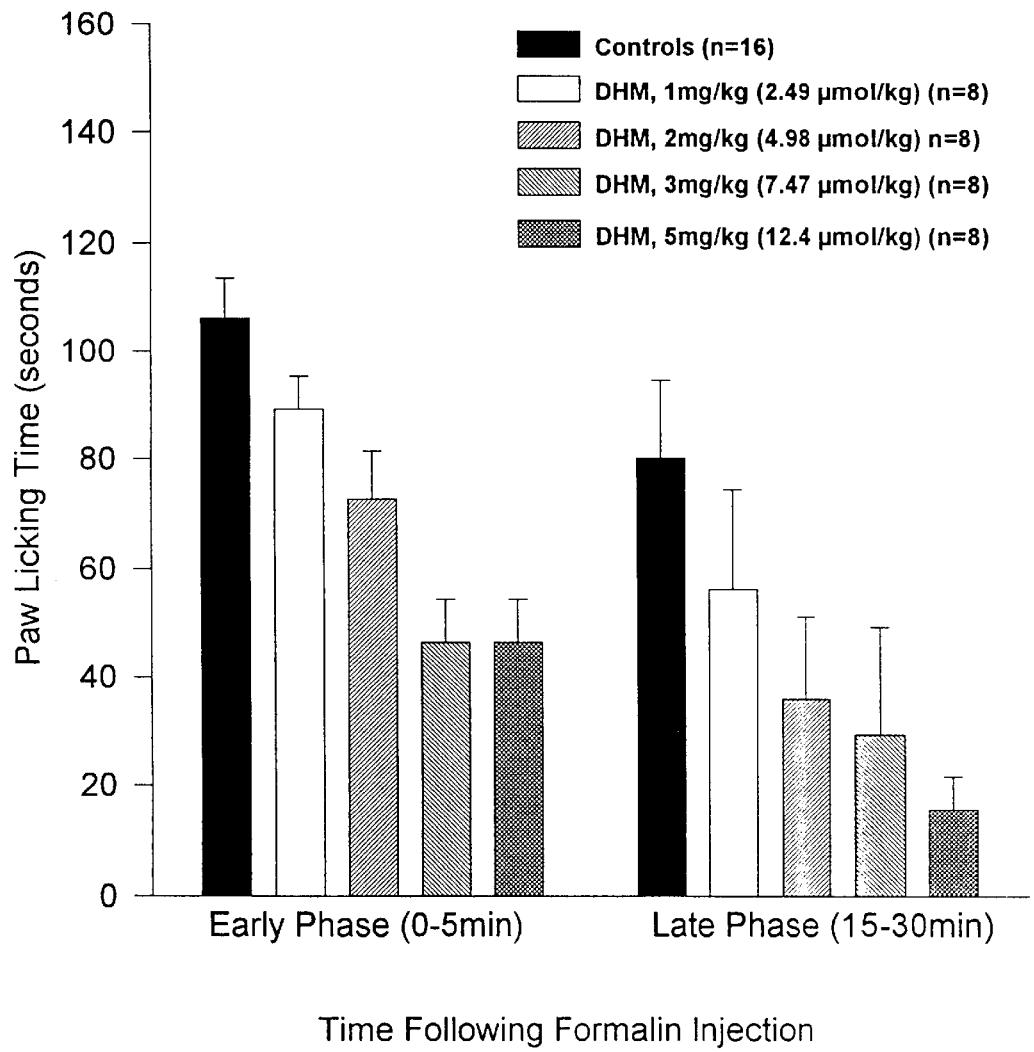
FIG. 1 shows the effect of dihydromorphine (DHM) on paw licking time following formalin injection.

The present invention provides further embodiments of the heterodimeric compounds described in this application's progenitors. The invention may be generally described by the formula:

(BKAn)(X)(Y)

where the terms BKAn, X and Y are as previously defined. According to the present invention, the mu-opioid agonist is selected from fentanyl, dihydromorphine, and morphine or derivatives or analogues thereof.

According to a particular embodiment, Y is

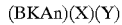

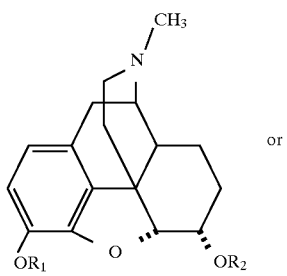

-continued

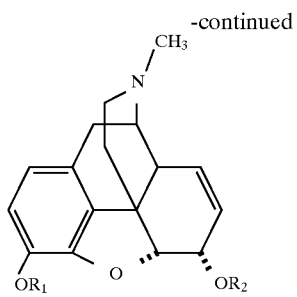

where R1 and R2 are independently selected from

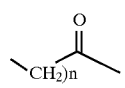 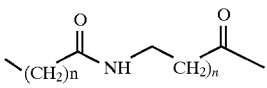

where n = 1 to 20    where n = 1 to 15

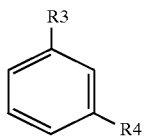  or  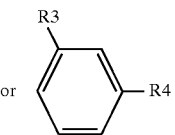

where R3 is (CH₂)n where n = 1 to 4 and
R4 is C(O); CO₂C(O); CONH(CH₂)₂C(O) or
CONH(CH₂)₂CONH(Phe)CH₂C(O)

(which represent the linker group X) or H.

In another preferred embodiment, Y is

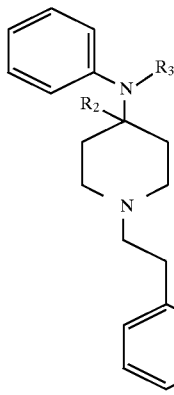 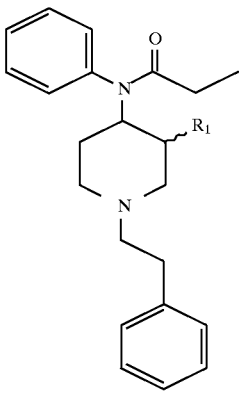

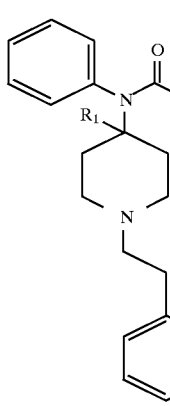 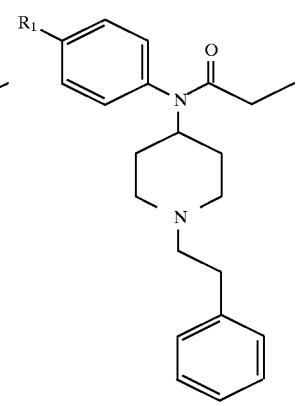

-continued

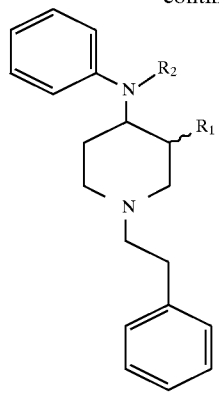

or

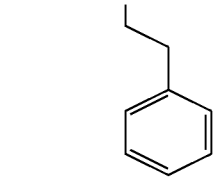

where R1 and R2 are independently selected from

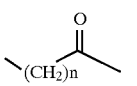 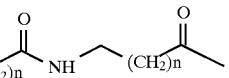

where n = 1 to 20    where n = 1 to 15

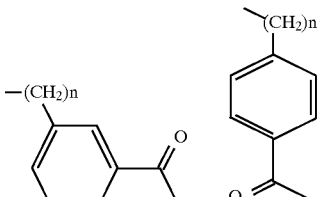

where n = 1 to 4    where n = 1 to 4

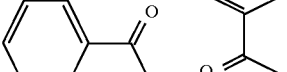

where n = 1 to 6    where R3 NHC(O)(CH₂)₂
R4 is C(O); CH₂C(O) or
CH₂C(O)NH(CH₂)₂C(O)

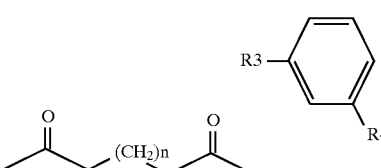

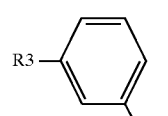

where R3 is CO(CH₂)₂NH— and
R4 is —CONH(CH₂)₂CO

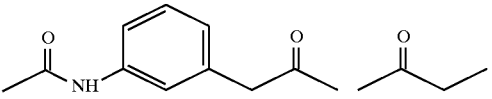

where R3 is (CH₂)₄NHCO— and
R4 is —CONH(CH₂)₂CO

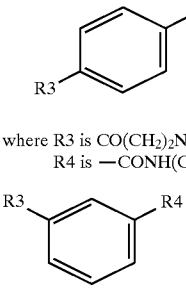

(which represent the linker group X) or H.

According to another embodiment, Y is

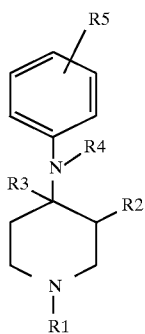

where
R1 is a linking group X of the formula $CH_2CH_2(Phe)CH_2CO$;
R2, R3, R5 are H; and
R4 is $COCH_2CH_3$
Preferred BKAn components include
D-Arg-Arg-Pro-Hyp-Gly-Iglb-Ser-D-Iglb-Oic-Arg (B9430);
D-Arg-Arg-Pro-Hyp-Gly-Thi-Ser-D-Iglb-Oic-Arg (B9340);
D-Arg-Arg-Pro-Hyp-Gly-Thi-Ser-D-Tic-NChg-Arg (CP-0597);
D-Arg-Arg-Pro-Hyp-Gly-Phe-Ser-D-Tic-NChg-Arg;
D-Arg-Arg-Pro-Hyp-Gly-Iglb-Ser-D-Iglb-Iglb-Arg;
D-Arg-Arg-Pro-Hyp-Gly-Thi-Ser-D-Tic-Oic-Arg (HOE-140);
D-Arg-Arg-Pro-Hyp-Gly-Phe-Ser-DHypTE-Oic-Arg;

or analogs thereof provided that such analogs possess bradykinin antagonist activity.

In addition, it is contemplated that any of the above peptides may be substituted with L-Arg or L-Lys in the "0" position (i.e., D-Arg). The peptides may be also substituted with D- or L-Lys in the 0 to 6 positions for coupling to Y. Linkage may then be accomplished, for example, via the ∝-amino group of the L-Arg, D-Lys or L-Lys residue.

Also described herein are the following compounds:

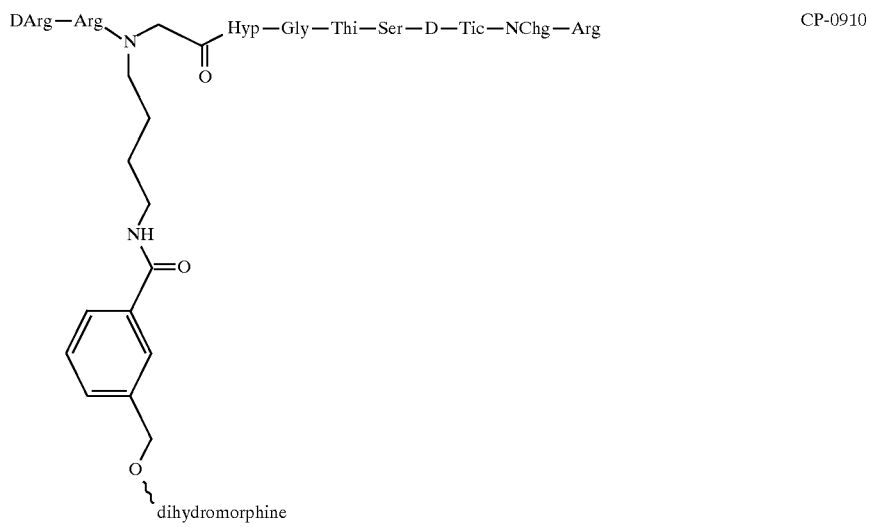

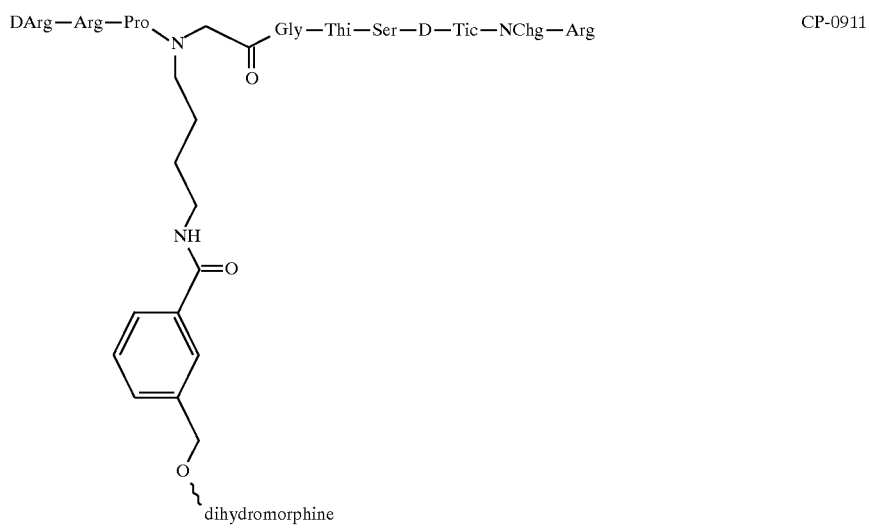

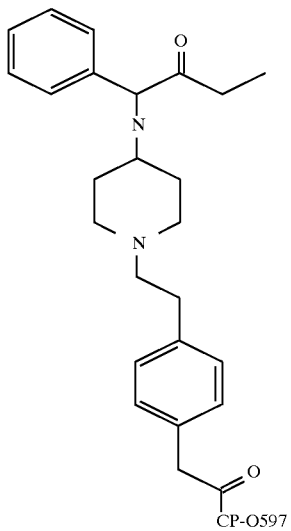

CP-O597

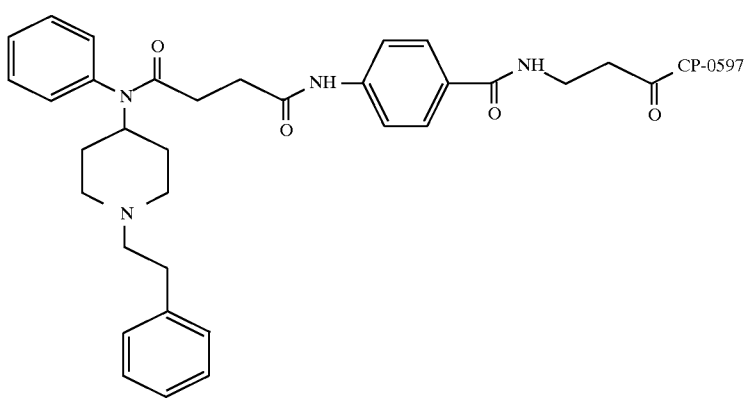

CP-0913

As used herein, the symbol

" ~ "

indicates a stereoisomeric mixture.

As used herein, abbreviations of the natural amino acids are those accepted in the art (*Biochem J.* 126:773 (1972)), and unless prefixed with D- are all of the L-configuration (except glycine, which is not optically active).

Abbreviations used for unnatural amino acids in Bradykinin analogs are indicated below:

Iglb α-(2-indanyl)glycine)
Hyp trans-4-Hydroxy-Pro
D-HypTE D-hydroxyproline trans thiophenyl ether
Thi β-2-Thienyl-Ala
D-Tic D-(1, 2, 3, 4-tetra hydroisoquinolin-3-yl-carbonyl)
Oic Cis-endo-octahydroindo-2-carbonyl
NChg N-(cyclohexyl)glycine

EXAMPLES

Example I 4,5α-Epoxy-6-α-hydroxy-3-O-(12-carboxydodecanoic acid)-7,8-dihydro-17-methylmorphinan To a solution containing 1.8 g (3.32 mmol) of 4,5α-Epoxy-6-α-hydroxy-3-O-(12-carbo-t-butoxydodecanoic acid)-7,8-dihydro-17-methylmorphinan in 40 ml of ethanol and 12 ml of water was added 0.98 g (16.09 mmol) of potassium hydroxide. The mixture was heated to reflux for 4 hours. The reaction mixture was diluted with water and washed with methylene chloride. The aqueous phase was acidified with 1N aqueous hydrochloric acid and extracted with methylene chloride. The organic phase was dried over magnesium sulfate. Filtration and removal of solvent afforded 1.38 g (85.59%) of product as a white solid.

$^1$H NMR (CDCl$_3$)δ 1.28 (bs, 14H), 1.28–1.48 (m, 5H), 1.60–1.80 (m, 6H), 2.13 (m, 1H) 2.28 (t, J=7.4 Hz, 2H), 2.50 (m, 2H), 2.62 (s, 3H), 2.70 (dd J1=6.0 Hz, J2=19.4 Hz, 1H), 3.01 (d, J=19.1 Hz, 1H), 3.02 (m, 1H), 3.49 (m, 1H), 4.05 (m,3H), 4.60 (d, J=5.5 Hz, 1H), 6.64 (d, J=8.2 Hz, 1H), 6.75 (d, J=8.2 Hz, 1H).

$^{13}$C NMR (CDCl$_3$)δ 18.27, 20.88, 25.56, 25.89, 27.36, 29.31, 29.36, 29.47, 35.25, 35.69. 38.84, 40.91, 41.35, 46.78, 59.96, 66.60, 69.55, 89.53, 115.46, 119.31, 123.90, 129.21, 141.51, 146.50, 178.65

| $C_{29}H_{43}N_1O_5H_2O$ | % C | % H | % N |
|---|---|---|---|
| Theory | 69.15 | 9.01 | 2.78 |
| Found | 69.08 | 8.80 | 2.53 |

The intermediate 4,5α-Epoxy-6-α-hydroxy-3-O-(12-carbo-t-butoxy dodecanoic acid)-7,8-dihydro-17-methylmorphinan was prepared as follows:

a) 4,5α-Epoxy-3-O-acetyl-6-α-hydroxy-7,8-didehydro-17-methylmorphinan

To a solution containing 15.0 g (19.77 mmol) of morphine sulfate pentahydrate in 1.2 L of water was added 56.4 g (672.06 mmol) of sodium bicarbonate. After stirring for 10 minutes, 28.0 ml (296.26 mmol) of acetic anhydride was added and stirring continued for 45 minutes. The reaction mixture was transferred to a separatory funnel and extracted with chloroform (3×). The organic phase was dried over calcum sulfate. Filtration and removal of solvent afforded 12.9 g (100%) of product as a white solid.

$^1$H NMR (CDCl$_3$)δ 1.86–1.95 (m, 1H), 2.07 (dt, J1=5.1 Hz, J2=12.5 Hz, 1H), 2.26–2.42 (m, 2H), 2.30 (s, 3H), 2.44 (s, 3H), 2.58 2.71 (m, 2H), 3.05 (d, J=18.7 Hz, 1H) 3.35 (dd, J1=3.3 Hz, J2=6.0 Hz, 1H), 4.15–4.20 (m, 1H), 4.92 (d, J=6.6 Hz, 1H), 5.28 (dt, J1=2.6 Hz, J2=10.4 Hz, 1H), 5.72–5.82 (m, 1H), 6.61 (d, J=8.1 Hz, 1H), 6.74 (d, J=8.1 Hz, 1H).

$^{13}$C NMR (CDCl$_3$)δ 20.57, 34.97, 40.15, 42.42, 42.82, 46.16, 58.66, 65.66, 92.13, 119.66, 120.88, 127.56, 131.56, 132.07, 132.59, 133.95, 148.56, 168.37.

b) 4,5-α-Epoxy-6-α-0-acetyl-3-O-(12-carbo-t-butoxydodecanoicacid)-7,8-didehydro-17-methylmorphinan To a solution containing 2.5 g (7.64 mmol) of 4,5α-Epoxy-3-O-acetyl-6-α-hydroxy-7,8-didehydro-17-methylmorphinan in 40 ml of dimethylformamide under a nitrogen atmosphere was added 0.2 g (8.33 mmol) of sodium hydride. After complete gas evolution, a solution containing 2.71 g (8.08 mmol) of 12-bromo-dodecanoic acid t-butylester in 8 ml of dimethylformamide was added. The reaction was heated to 50° C. and maintained for 1 hour 45 minutes while monitoring by thin layer chromatography. The reaction mixture was diluted with ethyl acetate and washed with water. The organic phase was dried over magnesium sulfate. Filtration, removal of solvent, and column chromatography of the residue on silica gel with 20% methanol/methylene chloride afforded 3.79 g (85.27%) of product as a viscous oil.

$^1$H NMR (CDCl$_3$)δ 1.23–1.37 (m,14H), 1.44 (S, 9H), 1.52–1.62 (m, 2H), 1.68–1.90 (m,3H), 2.15 (s, 3H), 2.20 (t, J=7.4 Hz, 2H) 2.25–2.40 (m, 2H), 2.45 (s, 3H), 2.54–2.64 (m, 1H), 2.74 (bs, 1H) 3.03 (d, J=18.5 Hz, 1H), 3.32–3.40 (m,1H), 3.94–4.06 (m, 2H), 5.07 (d, J=6.0 Hz, 1H), 5.15–5.20 (m, 1H), 5.44 (dt, J1=2.4 Hz, J2=10.2 Hz, 1H), 5.60–5.65 (m, 1H), 6.52 (d, J=8.1 Hz, 1H), 6.66 (d, J=8.1 Hz, 1H).

c) 4,5α-Epoxy-6α-0-acetyl-3-O-(12-carb-t-butoxydodecanoicacid)-7,8-didehydro-17-methylmorphinan A solution containing 3.70 g (6.36 mmol) of 4,5α-Epoxy-6α-0-acetyl-3-O-(12-carbo-t-butoxydodecanoic acid)-7,8-didehydro-17-methylmorphinan in 100 ml of ethanol was charged with 0.6 g of 10% palladium on carbon and pressurred with hydrogen to 40 psig. The flask was shaken for 24 hours. The reaction mixture was then filtered through a plug of celite and the solvent removed under reduced pressure. Column chromatography of the residue on silica gel with 20% methanol/methylene chloride afforded 3.19 g (85.91%) of product.

$^1$H NMR (CDCl$_3$)δ 1.27 (bs, 14H), 1.44 (s, 9H), 1.38–1.92 (m, 8H), 1.78 (s, 3H), 2.25 (t, J=7.7 Hz, 2H), 2.25–230 (m, 4H), 2.41 (s, 3H), 2.36–2.45 (m, 1H), 2.51–2.57 (m, 1H), 2.99 (d, J=18.4 Hz, 1H), 3.11 (dd, J1=2.3 Hz, J2=5.0 Hz, 1H), 3.93–4.13 (m, 2H), 4.60 (d, J=5.9 Hz, 1H), 5.29–5.34 (m, 1H), 6.59 (d, J=8.2 Hz, 1H), 6.69 (d, J=8.2 Hz, 1H).

$^{13}$C NMR (CDCl$_3$)δ 19.14, 20.11 20.61 25.07, 25.96, 26.04, 28.07, 29.05, 29.25, 29.41, 29.49, 29.62, 35.59, 36.58, 41.44, 41.99. 42.79, 47.11, 59.64, 67.94, 69.69. 79.84. 87.15, 115.33. 118.77, 126.29, 129.56, 141.11, 146.85. 170.56, 173.33.

d) 4,5α-Epoxy-6-α-hydroxy-3-O-(12-carbot-butoxydodecanoic acid)-7,8-dihydro-17-methylmorphinan To a solution containing 3.0 g (5.14 mmol) of 4,5α-Epoxy-6-α-0-acetyl-3-O-(12-carbo-t-butoxy-dodecanoic acid)-7,8-dihydro-17-methylmorphinan in 75 ml of methanol and 9 ml of water was added 0.92 g (6.66 mmol) of potassium carbonate. After stirring overnight at room temperature, the reaction was diluted with ethylacetate and washed with water. The organic phase was dried over sodium sulfate. Filtration, removal of solvent, and column chromatography of the residue on silica gel with 30% methanol/methylene chloride afforded 2.46 g (88.33%) of product.

$^1$H NMR (CDCl$_3$)δ 1.27 (bs 14H), 1.44 (s, 9H), 1.37–1.83 (m, 8H), 1.90 (dt, J1=5.0 Hz, J2=12.4 Hz, 1H), 2.20 (t, J=7.3 Hz, 2H), 2.24–2.31 (m, 3H), 2.36–2.45 (m, 1H), 2.41 (s, 3H), 2.53–2.58 (m, 2H) 2.99 (d, J=18.5 Hz, 1H), 3.11 (dd, J1=2.8 Hz, J2=5.5 Hz, 1H), 3.98–4.07 (m, 3H), 4.59 (d, J=5.4 Hz, 1H) 6.61 (d, J=8.2 Hz, 1H), 6.72 (d, J=8.2 Hz, 1H)

$^{13}$C NMR (CDCl$_3$)δ 19.01, 20.05, 25.05, 25.91, 27.16, 28.06, 29.02, 29.22, 29.35, 29.39, 29.46, 35.56, 37.07, 42.40, 41.91, 42.81, 46.83, 59.76, 67.04, 69.50, 79.83, 90.20, 114.81, 119.09, 126.52, 130.17, 140.92, 146.42, 173.33.

Example II

Heterodimer of 4,5α-Epoxy-6-α-hydroxy-3-O-(12-carboxy dodecanoic acid)-7,8-dihydro-17-methylmorphinan and CP-0597

To a solution containing HBTU (10.8 mg, 0.028 mmol) in 1.5 ml of DMF was added CP-0597 (25 mg, 0.014 mmol) in 0.5 ml of DMF. The mixture was stirred at room temperature and after 0.5 hours half of a solution containing 4,5α-Epoxy-6-α-hydroxy-3-O-(12-carboxydodecanoic acid)-7,8-dihydro-17-methylmorphinan (13.9 mg, 0.029 mmol), 20 μl DIEA in 0.5 ml DMF was added. After 2.0 hours the remainder of the carboxylic acid mixture was added and the mixture allowed to stir for an additional 3.0 hours. The resulting mixture was diluted with 50 ml of Et$_2$O and placed at 0° C. overnight. The ether was decanted and washed again with Et$_2$O. The resulting isolated material was dissolved into CH$_3$CN/H$_2$O 7:3 containing 10% AcOH and purified using RP-HPLC (9:1 to 2:3 H$_2$O:CH$_3$CN+0.1% TFA over 60 minutes). The five fractions were combined, evaporated and lyophilized to give 12.3 mg of 3-O-alkylated dihydromorphine and CP-0597 heterodimer as a white powder.

Analysis: The mass spectra was run on a Finnigan Lasermat Mass Analyzer: calculated (M+H) 1761, found (M+H) 1761.

Amino Acid Analysis: Arg 3.08 (3), Pro 1.44 (1), Hyp 0.88 (1); Gly 0.92 (1), Ser 0.90 (1).

Amino Acid Sequencing: Gave no residues.

Example III 4,5α-Epoxy-3-hydroxy-6-α-O-(benzyl-3-carboxylic acid)-7,8-didehydro-17-methylmorphinan To a solution containing 0.08 g (0.18 mmol) of 4,5-α-Epoxy-3-hydroxy-6-α-0-(benzyl-3-carboxymethyl ester)-7,8-didehydro-17-methylmorphinan in 5.5 ml of methanol and 2 ml of water was added 0.03 g (0.71 mmol) of lithium hydroxide monohydrate. After stirring at room temperature overnight, the solvent was removed under reduced pressure. The residue was dissolved in water and filtered. Purification via RP-HPLC afforded 81.6 mg (84.97%) of product as a white solid after lyophilization.

$^1$H NMR (CDCl$_3$)δ 2.05–2.14 (m, 1H), 2.43–2.62 (m, 2H), 2.83–2.93 (m, 1H), 2.93 (s, 3H), 3.11 (d, J=22 Hz, 1H), 3.23 (s, 1H), 3.40–3.48 (m, 2H), 4.08 (bs, 2H), 4.73 (d, J=11.8 Hz, 1H), 4.88 (d, J=11.9 Hz, 1H), 5.12 (d, J=6.1 Hz, 1H), 5.32 (d, J=10.2 Hz, 1H), 5.91 (d, J=10.1 Hz, 1H), 6.54 (d, J=8.5 Hz, 1H), 6.73 (d, J=8.2 Hz, 1H), 7.46 (t, J=7.5 Hz, 1H), 7.64 (d, J=7.6 Hz, 1H), 8.02 (d, J=7.6 Hz, 1H), 8.19 (bs, 1H).

LRMS calculated for C$_{25}$H$_{25}$N$_1$O$_5$:419.17. Found 420 (M+1)

The intermediate 4,5∝-Epoxy-3-hydroxy 6-∝-O-(benzyl-3-carboxymethyl ester)-7,8-didehydro-17-methylmorphinan was prepared as follows:

a) 4,5-∝-Epoxy-3-triphenylmethoxy-6-∝-hydroxy-7,8-didehydro-17-methylmorphinan

To a mixture containing 24.0 g (31.64 mmol) morphine sulfate pentahydrate, 15.90 g (57.03 mmol) of triphenylmethyl chloride, and 5.50 g (16.20 mmol) of tetrabutylammonium hydrogen sulfate in 400 ml of methylene chloride was added 400 ml (136.00 mmol) of 0.34M potassium hydroxide. The reaction was allowed to stir vigorously at room temperature overnight.

The reaction mixture was diluted with methylene chloride and the organic phase separated. The aqueous phase was further extracted with methylene chloride. The combined organic layers were dried over magnesium sulfate. Filtration, removal of solvent, and column chromatography of the residue on silica gel with 5% methanol/methylene chloride, then 20% methanol/methylene chloride afforded 14.20 g (42.53%) of product as white solid.

$^1$H NMR (CDCl$_3$)δ 1.57–1.66 (m, 1H), 1.92 (dt, J1=4.8 Hz, J2=12.4 Hz, 1H), 2.10–2.32 (m, 3H), 2.39 (s, 3H), 2.43–2.60 (m, 2H), 2.89 (d, J=18.7 Hz, 1H), 3.24 (dd, J1=3.9 Hz, J2=6.1 Hz, 1H), 3.98 (bs, 1H) 4.60 (d, J=6.6 Hz, 1H), 5.16 (dt, J1=3.0 Hz, J2=9.9 Hz, 1H), 5.45–5.53 (m, 1H), 6.17 (d, J=8.3 Hz, 1H), 6.35 (d, J=8.2 Hz, 1H), 7.20–7.45 (m, 15H).

$^{13}$C NMR (CDCl$_3$)δ 20.57, 35.51, 40.45, 42.54, 42.99, 46.32, 58.82, 66.18, 90.54, 118.60, 123.61, 127.25, 127.43, 127.79, 129.36, 133.36, 137.76, 144.21, 150.65.

LRMS calculated for C$_{36}$H$_{35}$N$_1$O$_3$:527.25; found: 528 (M+1)

b) 4,5-∝-Epoxy-3-triphenylmethoxy-6-∝-O-(benzyl-3-carboxymethyl ester)-7,8-didehydro-17-methylmorphinan To a solution containing 2.50 g (4.74 mmol) of 4,5-∝-Epoxy-3-triphenylmethoxy-6-∝-hydroxy-7,8-didehydro-17-methylmorphinan in 30 ml of dimethylformamide under a nitrogen atmosphere was added 0.13 g (5.21 mmol) of sodium hydride and 1.19 g (5.21 mmol) of methyl-3-bromomethylbenzoate. The reaction mixture was heated to 50° C. and maintained for 24 hours. The reaction mixture was diluted with ethylacetate and washed with brine, then water. The organic phase was dried over magnesium sulfate. Filtration, removal of solvent, and column chromatography of the residue on silcia gel with a 5%–10% methanol/methylene chloride gradient afforded 0.19 g (6.00%) of product.

$^1$H NMR (CDCl$_3$)δ 1.50–2.60 (m, 6H), 2.30 (s, 3H), 2.87 (d, J=19.1 Hz, 1H), 3.26 (bs, 1H), 3.91 (s, 3H), 3.93 (bs, 1H), 4.54 (d, J=12.0 Hz, 1H), 4.78 (d, J=6.4 Hz, 1H), 4.83 (d, J=11.6 Hz, 1H), 5.21 (d, J=9.6 Hz, 1H), 5.69 (d, J=9.7 Hz, 1H), 6.11 (d, J=8.5 Hz, 1H), 6.34 (d, J=8.0 Hz, 1H), 7.00–7.47 (m, 18H), 7.55 (d, J=7.6 Hz, 1H) 7.95 (d, J=7.6 Hz, 1H), 8.03 (bs, 1H).

c) 4,5-∝-Epoxy-3-hydroxy-6-∝-O-(benzyl-3-carboxymethylester)-7,8-didehydro-17-methylmorphinan To a solution containing 0.19 g (0.28 mmol) of 4,5-∝-Epoxy-3-triphenylmethoxy-6-∝-O-(benzyl-3-carboxymethyl ester)-7,8-didehydro-17-methylmorphinan in 8 ml of methanol and 2 ml of methylene chloride was added 0.057 g (0.30 mmol) of p-toluenesulfonic acid monohydrate. After stirring at room temperature for 0.5 hours, the solution was diluted with methylene chloride and washed with a saturated sodium bicarbonate solution. The organic phase was dried over magnesium sulfate. Filtration and removal of solvent afforded the desired product which was utilized in the subsequent step.

Example IV

Heterodimer of 4.5-∝-Epoxy-3-hydroxy-6-∝-O-(benzyl-3-carboxyl acid)-7,8-didehydro-17-morphinan and CP-0597 (CP-0903)

To a solution containing HBTU (6.1 mg, 0.016 mmol) in DMF (0.5 ml) and 20 μL of DIEA was added 8.54 g (0.010 mmol) of 4,5∝-Epoxy-3-hydroxy-6-∝-O-(benzyl)-3-carboxylic acid-7,8-didehydro-17-methylmorphinan from Example 3. After 0.5 hours, this mixture is added to a solution of CP-597 (20 mg, 0.011 mmol) in 1.5 ml DMF and this resulting mixture stirred for 4 hours. This mixture was diluted with cold Et$_2$O, centrifuged and decanted. The resulting material was dissolved into 10% AcOH in H$_2$O and purified by RP-HPLC (9:1 to 2:3 H$_2$O:CH$_3$CN containing 0.1% TFA over 50 minutes). The desired fractions were combined, evaporated and lyophilized to give 12.1 mg of 6-O-alkylated morphine and CP-0597 heterodimer as a white powder.

Mass Spectral Analysis: calculated (M+2) 1695; found (M+2) 1695.

Example V

N-phenyl-N-[1-(2-phenethyl)-4-piperidinyl]-9-carboxyl nonamide

To a solution containing 1.50 g (3.23 mmol) of N-phenyl-N-[1-(2-phenethyl)-4-piperidinyl]-9-carbomethoxy nonamide in 30 ml of methanol and 10 ml of water was added 0.20 g (4.77 mmol) of lithium hydroxide monohydrate under a nitrogen atmosphere. After stirring at room temperature for 24 hours, the reaction mixture was diluted with methylene chloride and acidified with 1N aqueous hydrochloric acid. The organic phase was separated and dried over magnesium sulfate. Filtration, removal of solvent, and column chromatography of the residue on silica gel with 10% methanol/methylene chloride afforded 0.85 g (58.4%) of product as a white solid.

$^1$H NMR (CDCl$_3$)δ 1.17–1.30 (m, 6H), 1.42–1.54 (m, 4H), 1.63–1.76 (m, 2H), 1.77–1.95 (m, 4H), 2.13 (t, J=7.4 Hz, 2H), 2.49 (t, J=11.7 Hz, 2H), 2.82–2.92 (m, 4H), 3.35 (d, J=10.8 Hz, 2H), 4.65–4.85 (M, 1H), 7.05–7.08 (m, 2H), 7.15–7.29 (m, 5H), 7.34–7.41 (m, 3H), 12.16 (bs, 1H).

$^{13}$C NMR (CDCl$_3$)δ 25.06, 25.30, 28.59, 28.88, 28.92, 28.96, 31.60, 34.85, 50.90, 52.11, 58.75, 126.52, 128.55, 128.59, 129.45, 129.99, 138.10, 138.25, 173.17, 177.81. C$_{28}$H$_{38}$N$_2$O$_3$H$_2$O

|  | % C | % H | % N |
|---|---|---|---|
| Theory | 71.76 | 8.60 | 5.98 |
| Found | 72.05 | 8.61 | 5.89 |

The intermediate N-phenyl-N-[1-(2-phenethyl)-4-piperidinyl]-9-carbomethoxynonamide was prepared as follows:

a) N-(phenylamine)-1-(2-phenethyl)piperidine

A solution containing 5.0 g (24.60 mmol) of 1-phenethylpiperidine, 13.60 ml (149.24 mmol) of aniline and 9.80 ml (49.20 mmol) of 5N hydrochloric acid in methanol was stirred at room temperature while 0.92 g (14.64 mmol) of sodium cyanoborohydride was added followed by 30 g of 3A° molecular sieves. The reaction was allowed to stir at room temperature for 3 days. The reaction mixture was filtered and the solvent removed under reduced pressure. The residue was disolved in ether and washed with water. The organic phase was dried over magnesium sulfate. Filtration, removal of solvent, and column chromatography of the residue on silica gel with 10% methanol/methylene chloride afforded 4.51 g (65.38%) of product as pale yellow solid.

$^1$H NMR (CDCl$_3$)δ 1.42–1.56 (m, 2H), 2.08 (d, J=12.4 Hz, 2H), 2.19 (t, J=11.2 Hz, 2H), 2.57–2.63 (m, 2H), 2.78–2.84 (m, 2H), 2.93–2.97 (m, 2H), 3.31 (bs, 1H), 3.51 (bs, 1H), 6.59 (d, J=7.6 Hz, 2H), 6.67 (t, J=7.3 Hz, 1H), 7.13–7.31 (m, 7H).

$^{13}$C NMR (CDCl$_3$)δ 32.51, 33.84, 49.84, 52.38, 60.55, 113.17, 117.13, 125.97, 128.32, 128.61, 129.24, 140.32, 147.02.

b) N-phenyl-N-[1-(2-phenethyl)-4-piperidinyl]-9-carbomethoxynonamide

To a solution containing 1.0 g (3.57 mmol) of 4-(phenylamine)-1-(2-phenethyl)piperidine in 20 ml of methylene chloride was added 1.2 g (5.44 mmol) of the acid chloride of azelaic acid monomethylester under a nitrogen atmosphere at 0° C. The reaction was allowed to warm to room temperature overnight. The reaction mixture was diluted with methylene chloride and washed with a saturated sodium bicarbonate solution. The organic phase was dried over magnesium sulfate. Filtration, removal of solvent, and column chromatography of the residue on silica gel with 10% methanol/methylene chloride afforded 1.60 g (97.06%) of product.

$^1$H NMR (CDCl$_3$)δ 1.12–1.62 (m, 12H), 1.78–1.82 (m, 2H), 1.90 (t, J=7.1 Hz, 2H), 2.16 (t, J=11.7 Hz, 2H), 2.18–2.31 (m, 2H), 2.50–2.56 (m, 2H), 2.70–2.76 (M, 2H), 3.00 (bd, J=11.6 Hz, 2H), 3.65 (s, 3H), 4.68 (tt, J1=4.0 Hz, J2=12.1 Hz, 1H), 7.05–7.42 (m, 10H).

$^{13}$C NMR (CDCl$_3$)δ 24.78, 25.29, 28.83, 28.86, 28.96, 30.53, 33.77, 33.96, 34.84, 51.33, 52.08, 53.05, 60.40, 125.94, 128.18, 128.29, 128.55, 129.19, 130.38, 138.84, 140.18, 172.67.

Example VI

Heterodimer of N-phenyl-N-[1-(2-phenethyl)-4-piperidinyl-9-carboxyl nonamide and CP-0597 (i.e. CP-0719)

This heterodimer of the fentanyl analogue N-phenyl-N-[1-(2-phenethyl)-4-piperidinyl]-9-carboxyl nomamide and CP-0597 was prepared by a similar coupling procedure as described in Example 4. The crude material was dissolved up into H$_2$O/CH$_3$CN/AcOH (8:2:1) and purified by RP-HPLC (9:1 to 2:3 H$_2$O:CH$_3$CN containing 0.1% TFA over 60 minutes). The pure fractions were combined, evaporated and lyophilized to give 14.0 mg of the heterodimer.

Mass Spectral Analysis: calculated (M+1) 1726; found (M+1) 1726. Amino Acid Analysis: Arg 3.1 (3), Pro 0.91 (1), Hyp 1.12 (1), Gly 1.0 (1), Ser 0.98 (1), Thi 0.93 (1).

Example VII

N-(4-phenylacetic acid)-N-[1-(2-phenethyl)-4-piperidinyl]propanamide

To a solution containing 1.21 g (2.96 mmol) of N-(4-phenylacetic acid methyl ester)-N-[-1-(2-phenethyl)-4-piperidinyl]propanamide in 40 ml of methanol and 10 ml of water was added 0.25 g (5.96 mmol) of lithium hydroxide monohydrate under a nitrogen atmosphere. The mixture was heated to 50° C. After 2 hours, the methanol was removed under reduced pressure. The aqueous residue was purified via RP-HPLC to afford 1.39 g (92.34%) of product as a white solid and TFA salt after lyophilization.

$^1$H NMR (DMSOd$_6$)δ 0.99 (t, J=7.4 Hz, 3H), 1.75–1.85 (m, 2H), 1.92–2.01 (m, 4H), 2.90–3.04 (m, 4H), 3.15–3.21 (m, 2H), 3.62 (bs, 4H), 4.70–4.88 (m, 1H), 7.02 (d, J=8.3 Hz, 2H), 7.16–7.32 (m, 5H), 7.38 (d, J=8.2 Hz, 2H), 12.30 (bs, 1H).

$^{13}$C NMR (DMSOd$_6$)δ 8.72, 26.92, 27.58, 29.60, 40.01, 48.63, 51.16, 57.02, 126.40, 127.89, 128.09, 128.96, 129.96, 134.96, 135.46, 171.06, 172.95.

LRMS calculated for C$_{24}$H$_{30}$ N$_2$O$_3$ 394.22. Found 395 (M+1).

The intermediate N-(4-phenylaceticacidmethylester)-N-[1-(2-phenethyl)-4-piperidinyl]propanamide was prepared as follows:

a) 4-(4-carbomethoxymethylphenyl amine)-1-(2-phenethyl) piperidine

To a solution containing 5.0 g (24.60 mmol) of 1-phenethylpiperidine, 9.92 g (49.19 mmol) of 4-aminophenylacetic acid methyl ester and 9.8 ml (49.00 mmol) of 5N hydrochloric acid in methanol in 50 ml of methanol under a nitrogen atmosphere was added 0.92 g (14.64 mmol) of sodium cyanoborohydride followed by the addition of 30 g of 3A° molecular sieves. After stirring at room temperature for 72 hours, the reaction mixture was filtered through a plug of celite and the solvent removed under reduced pressure. The residue was dissolved in ether and washed with water. The organic phase was dried over magnesium sulfate. Filtration, removal of solvent, and column chromatography of the residue on silica gel with 10% methanol/methylene chloride afforded 1.49 g (17.14%) of product.

$^1$H NMR (CDCl$_3$)δ 1.44–1.58 (m, 2H), 2.05–2.11 (m, 2H), 2.22 (dt, J1=2.0 Hz, J2=11.5 Hz, 2H), 2.59–2.65 (m, 2H), 2.80–2.85 (m, 2H), 2.94–3.00 (m, 2H), 3.22–3.36 (m, 1H), 3.50 (s, 2H), 3.67 (s, 3H), 6.55 (d, J=8.6 Hz, 2H), 7.07 (d, J=8.6 Hz, 2H), 7.18–7.35 (m, 6H).

b) N-(4-phenylacetic acid methylester)-N-[1-(2-phenethyl)-4-piperidinyl]propanamide To a solution containing 1.45 g (4.10 m mol) of 4-(4-carbomethoxymethyl phenylamino)-1-(2-phenethyl) piperidine in 40 ml of methylene chloride under a nitrogen atmosphere at 0° C., was added 0.55 ml (6.33 mmol) of propionylchloride. The reaction was allowed to warm to room temperature overnight. The mixture was diluted with methylene chloride and washed with water. The organic phase was dried over magnesium sulfate. Filtration, removal of solvent, and column chromatography of the residue on silica gel with 10% methanol/methylene chloride afforded 1.28 g (76.23%) of product.

¹H NMR (CDCl₃)δ 1.01 (t, J=7.4 Hz, 3H), 1.42 (dq, J1=3.3 Hz, J2=1.8 Hz, 2H), 1.72–1.86 (m, 2H), 1.93 (q, J=7.5 Hz, 2H), 2.15 (t, J=10.4 Hz, 2H), 2.50–2.56 (m, 2H), 2.70–2.76 (m, 2H), 3.00 (bd, J=11.6 Hz, 2H), 3.65 (s, 2H), 3.74 (s, 3H), 4.69 (tt, J1=4.1 Hz, J2=12.1 Hz, 1H), 7.03 (d, J=8.3 Hz, 2H), 7.13–7.29 (m, 5H), 7.31 (d, J=8.3 Hz, 2H).

¹³C NMR (CDCl₃)δ 9.58, 28.52, 30.56, 33.85, 40.65, 52.09, 52.16, 53.08, 60.48, 125.99, 128.35, 128.60, 130.17, 130.52, 134.23, 137.78, 140.24, 171.45, 173.48. $C_{25}H_{32}N_2O_3$

|  | % C | % H | % N |
|---|---|---|---|
| Theory | 73.50 | 7.89 | 6.86 |
| Found | 73.32 | 7.81 | 6.77 |

Example VIII

Heterodimer of N-(4-phenylacetic acid)-N-[1-(2-phenethyl)-4-piperidinyl]propanamide and CP-0597 (i.e. CP-0872)

This heterodimer of the fentanyl analogue N-(4-phenylacetic acid)-N-[1-(2-phenethyl-4-piperidinyl] propanamide and CP-0597 was prepared by a similar coupling method as described in Example IV. The crude heterodimer was dissolved into 10% AcOH/H₂O and purified on RP-HPLC (9:1 to 35:65 H₂O:CH₃CN containing 0.1% TFA over 30 minutes). Pure fractions were combined, evaporated and lyophilized to give 15.4 mg of the heterodimer, CP-0872, as a white powder.

Mass Spectral Analysis: found 1672

Example IX

N-phenyl-N-[1-(2-phenethyl)-4-carboxy-4-piperidinyl]propanamide

To a solution containing 0.50 g (1.14 mmol) of 4-phenylamine- 1-[2-phenethyl-4-carboxy]piperidine in 10 ml of methylene chloride and 0.23 ml (1.65 mmol) of triethylamine under a nitrogen atmosphere at 0° C. was added 0.16 ml (1.84 mmol) of propionyl chloride. The reaction was allowed to warm to room temperature overnight. The solvent was removed under reduced pressure. Column chromatography of the residue on silica gel with 20% methanol/methylene chloride afforded 0.40 (92.2%) of product.

¹H (DMSO d₆)δ 0.92 (t, J=7.50 Hz, 3H), 1.87 (q, J=7.4 Hz, 2H), 1.90–2.10 (m, 2H), 2.35–2.50 (m, 2H), 2.97–3.04 (m, 2H), 3.19–3.78 (m, 6H), 7.20–7.46 (m, 10H).

¹³C NMR (DMSO d₆)δ 7.63, 27.17, 28.57, 28.85, 47.84, 55.69, 58.38, 125.45, 127.18, 127.49, 128.03, 128.83, 135.03, 137.20, 172.27.

LRMS calculated for $C_{23}H_{28}N_2O_3$: 380.21. Found: 381 (M+1).

The intermediate 4-phenylamino-1-[2-phenethyl-4-carboxy]piperidine was prepared as follows:

a) 4-phenylamine-4-cyano-1-(2-phenethyl)piperidine

To a solution containing 14.6 g (71.82 mmol) of 1-(2-phenethyl)-4-piperidine and 6.6 ml (72.43 mmol) of aniline in 50 ml of glacial acetic acid was added a solution of 5.14 g (78.93 mmol) of potassium cyanide in 15 ml of water dropwise while maintaining the reaction temperature below 20° C. with an ice bath. After stirring at room temperature for 48 hours, the reaction mixture was poured into 80 g of ice containing 93 ml of concentrated ammonium hydroxide. The aqueous phase was decanted and the brown oil dissolved in chloroform and washed with water. The organic phase was dried over potassium carbonate. Filtration and removal of solvent afforded a brown solid. Recrystallization from isopropanol afforded 7.77 g (35.42%) of product.

¹H (CDCl₃)δ 1.94 (dt, J1=3.7, J2=13.7 Hz, 2H), 2.36 (dt, J1=2.5 Hz, J2=13.2 Hz, 2H), 2.48–2.56 (m, 2H), 2.63–2.69 (m, 2H), 2.75–2.82 (m, 2H), 2.87–2.95 (m, 2H), 3.65 (s, 1H), 6.90–6.95 (m, 3H), 7.18–7.35 (m, 2H).

¹³C NMR (CDCl₃)δ 33.75, 36.18, 49.34, 59.87, 117.90, 120.61, 121.02, 126.13, 128.42, 128.64, 129.30, 140.06, 143.28. $C_{20}H_{23}N_3$

|  | % C | % H | % N |
|---|---|---|---|
| Theory | 78.65 | 7.59 | 13.76 |
| Found | 78.39 | 7.69 | 13.74 | b) 4-phenylamine-1-[2-phenethyl-4-carboxamide] piperidine

To a mixture containing 5.42 g (17.75 mmol) of 4-phenylamine-4-cyano-1-(2-phenethyl)piperidine in 100 ml of ethanol was added 2.82 g (70.50 mmol) of sodium hydroxide followed by 7.6 ml (74.39 mmol) of 30% aqueous hydrogen peroxide. The reaction mixture was heated to reflux under a nitrogen atmosphere overnight. The reaction mixture was diluted with water and extracted with methylene chloride. The organic phase was dried over magnesium sulfate. Filtration, removal of solvent, and column chromatography of the residue on silica gel with 15% methanol/methylene chloride afforded 2.56 (44.59%) of product.

¹H NMR (CDCl₃)δ 1.96 (d, J=13.2 Hz, 2H), 2.12–2.21 (m, 2H), 2.35 (dt, J1=3.9 Hz, J2=13.4 Hz, 2H), 2.55–2.61 (m, 2H), 2.75–2.87 (m, 9H), 4.02 (s, 1H), 5.42 (d, J=2.3 Hz, 1H), 6.64 (d, J=7.6 Hz, 2H), 6.81 (t, J=7.3 Hz, 1H), 6.87 (bs, 1H), 7.16–7.30 (m, 7H).

c) 4-phenylamine-1-[2-phenethyl-4-carboxy]piperidine

A mixture containing 2.55 g (7.88 mmol) of 4-phenylamine-1-[2-phenethyl-4-carboxamide]piperidine and 1.33 g (23.70 mmol) of potassium hydroxide in 20 ml of ethylene glycol was heated to reflux for 4 hours. The reaction mixture was cooled with an ice bath and 10 ml (40 mmol) of 4N hydrochloric acid in dioxane added, followed by 100 ml of ether. The solid was filtered and further purified via RP-HPLC to afford 2.5 g (72.64%) of product after lypophilization.

LRMS calculated for $C_{20}H_{24}N_2O$: 324.18. Found: 325 (M+1)

Example X

Heterodimer of N-phenyl-N-[1-(2-phenethyl)-4-carboxy-4-piperidinyl]propanamide and CP-0597 (i.e. CP-0823)

This heterodime of the fentanyl derivative N-phenyl-N-[1-(2-phenethyl)-4-carboxy-4-piperidinyl]propanamide and CP-0597 was prepared by a similar coupling method as described in Example IV. The crude heterodimer was purifed on RP-HPLC. Pure fraction were combined. evaporated and lyophilized to give 2.3 mg of heterodimer CP-0823 as a white powder.

Mass Spectral Data: Calculated (M+1) 1654. Found (M+1) 1654.

Example XI

Extended 3-Substituted Fentanyl Analogue

To a solution of N-phenyl-3-(2-carboxy-ethyl)-N-[1-(2-phenyethyl)-4-piperidinyl]propanamide (1.25 g, 3.00 mmol)

and methyl 3-aminophenylacetate (0.74 g, 3.67 mmol) in 6 ml of DMF at 0° C. was added DIEA (2.13 ml; 12.24 mmol) and HBTU (1.62 g, 4.28 mmol). The resulting mixture was allowed to stir overnight, warming to room temperature. The mixture was diluted with EtOAc and washed with water (3×20 ml) and dried (MgSO$_4$). The solution was evaporated and purified on silica gel (EtOAc to 5% MeOH/EtOAc) to give 1.42 g (81%) of the coupled product as a mixture of cis/trans iomers.

To a solution at 0° C. containing 1.40 g (2.45 mmol) of the methyl ester in 12 ml of methanol was added a solution of 0.26 g (6.1 mmol) of lithium hydroxide monohydrate in 3 ml of water. The mixture was stirred, warming to room temperature overnight. This solution was acidified with 1N HCl and resulting solid filtered and washed with water. The solid was dried for 48 hours under vacuum to give 1.20 g (90.4%) of the desired phenyl acetic acid derivative. This material was used without further purification in the subsequent coupling step.

To a solution of the fentanyl phenyl acetic acid derivative (0.30 g, 0.553 mmol) and ethyl 3-amino propionate.HCl (0.102 g, 0.663 mmol) in 5 ml of DMF at 0° C. was added DIEA. After 10 minutes, HBTU (0.294 g, 0.775 mmol) was added over 5 minutes and the mixture allowed to warm to room temperature overnight. The resulting mixture was diluted with EtOAc, washed with water (3×20 ml) and dried (MgSO$_4$). The MgSO$_4$ was filtered and the solution evaporated to give the crude product that was purified on silica gel (9:1 EtOAc/MeOH), 0.300 g (83%). This ester was used in the subsequent hydrolysis step.

To a solution containing 290 mg (453 mmol) of previously prepared ester in MeOH (8 ml) at 0° C. was added a solution of lithium hydroxide monohydrate (46 mg, 1.10 mmol) in 2.0 ml of water. The mixture was allowed to warm to room temperature overnight. The methanol was evaporated and the resulting residue purified on RP-HPLC to give isomer A and a mixture of A and B. Analytical RP-HPLC Data (90:10 to 0:100) H$_2$O:CH$_3$CN+0.1% TFA linear gradient 25 minutes), YMC-AQ-302-5, 150×4.6 mm; Isomer A: 11.90 minutes, Isomer B: 12.70 minutes.

Isomer A:
$^1$H NMR (CDCl$_3$)δ 1.01 (t, J=7.1 Hz, 3H), 1.40–5.65 (m, 1H), 1.77–2.20 (m, 3H), 1.93 (q, J=7.4 Hz, 2H), 2.20–2.35 (m, 1H), 2.35–2.55 (m, 3H), 2.55–2.70 (m, 1H), 2.75–3.10 (m, 4H), 3.10–3.30 (m, 1H), 3.30–3.50 (m, 3H), 3.48–3.64 (m, 3H), 4.10 (d, J=10.8 Hz, 1H), 4.92 (brs, 1H), 6.14 (brs, 1H), 6.97 (d, J=7.6 Hz, 2H), 7.11 (d, J=7.2 Hz, 2H), 7.23–7.30 (m, 5H), 7.35–7.48 (m, 6H), 9.15 (brs, 1H), 10.10 (brs, 1H).
$^{13}$C NMR (CDCl$_3$)δ 9.60, 25.72, 27.50, 28.51, 30.51, 33.17, 34.07, 34.77, 36.56, 43.59, 51.92, 57.26, 58.72, 119.63, 121.22, 125.68, 127.47, 128.56, 129.03, 129.35, 129.64, 129.96, 130.20, 135.18, 135.35, 138.53, 171.16, 171.41, 175.35.
Mass Spectral Analysis: Calculated (M+1) 613. Found (M+1) 614.

The intermediate N-phenyl-3-(2-carboxyethyl)-N-[1-(2-phenethyl)-4-piperidinyl]propanamide was prepared as follows:
a) N-phenyl-3-(2-carbomethoxyethyl)-N-[1-(2-phenethyl)-4-piperdinyl]propanamide To a solution containing 1.50 g (4.09 mmol) of 4-(phenylamino)-3-(2-carbomethoxy)-1-(2-phenethyl) piperidine (prepared according to: Borne, et al. *J. Med. Chem.* 27:1271 (1984)) in 30 ml of methylene chloride under a nitrogen atmosphere at 0° C. was added 0.43 ml (4.9 mmol) of propionyl chloride. The reaction mixture was allowed to warm to room temperature overnight. The reaction was diluted with methylene chloride and washed with a saturated aqueous sodium bicarbonate solution. The organic layer was dried over magnesium sulfate. Filtration, removal of solvent, and column chromatography of the residue on silica gel with 5% methanol/methylene chloride afforded 1.64 g (94.96%) of product as a mixture of cis/trans isomers.
$^1$H (CDCl$_3$)δ [1.00 (t, J=7.5 Hz), 1.03 (t, J=7.4 Hz), 3H], 1.40–1.60 (m,2H), 1.71–2.00 (m, 3H), 2.09–2.60 (m, 8H), 2.67–2.76 (m, 2H), 2.98–3.10 (m, 2H), 3.69 (s, 3H), [4.32–4.42 (m), 4.56–4.70 (m), 1H], 7.13–7.50 (m, 10H).
b) N-phenyl-3-(2-carboxyethyl)-N-[1-(2-phenethyl)-4-piperidinyl]propanamide A solution containing 0.416 g (0.99 mmol) of N-phenyl-3-(2-carbomethoxyethyl)-N-[-1-(2-phenethyl)-4-piperidinyl]propanamide and 0.10 g (2.38 mmol) of lithium hydroxide monohydrate in 20 ml of methanol and 5 ml of water was allowed to stir at room temperature overnight. The solvent was removed under reduced pressure and the residue purified via RP-HPLC to afford 0.329 g (84.66%) of product as a white solid after lyophilization.
$^1$H NMR (CDCl$_3$)δ [0.98 (t, J=7.4), 1.00 (t, J=7.4), 3H], 1.49–1.52 (m, 1H), 1.80–2.10 (m,3H), 1.98 (q, J=7.4, 2H), 2.10–2.70 (m, 4H), 2.75–2.80 (m, 1H), 2.90–3.40 (m, 4H), 3.59 (d, J=11.3, 1H), 3.84 (d, J=12.1, 1H), [4.5 (bs), 4.85 (bs), 1H], 6.95–7.45 (m, 10H).
$^{13}$C NMR (CDCl$_3$)δ 9.54, 9.60, 25.04, 25.17, 27.38, 28.46, 28.91, 30.11, 30.32, 30.91, 31.11, 35.95, 51.78, 52.80, 55.83, 57.97, 58.79, 127.23, 128.60, 128.65, 128.95, 129.04, 129.51, 130.10, 136.05, 175.22, 175.58, 176.34, 176.84.
LMRS calculated for C$_{25}$H$_{32}$N$_2$O$_3$:408.24. Found 409 (M+1).

Example XII

Heterodimer of Extended 3-substituted Fentanyl Analogue (Isomer A) and CP-0597 (CP-0880)

This heterodimer of Isomer A from Example XI and CP-0597 was prepared by a similar coupling procedure as described in Example IV. The crude material was dissolved into 10% acetic acid/H$_2$O and purified on RP-HPLC (90:10 to 35:65, H2O:CH$_3$CN+0.1% TFA over 55 minutes) The desired fractions were combined, evaporated and lyophilized to give 18.4 mg of the fentanyl-CP-0597 heterodimer CP-0880 as a white powder.

Mass Spectral Analysis: Calculated (M+2) 1889. Found (M+2) 1889.

Example XIII

B2 Receptor Antagonist Activity

The compounds were assayed for B2 receptor antagonist activity on guinea pig ileum, according to the commonly accepted assay methods for bradykinin as described by Trautschold (Handbook of Experimental Pharmacology, Vol. 25, Springer-Verlag, pp 53–55 (1969)) for inhibition of the myotropic activity of bradykinin.

The inhibition potencies were determined according to the commonly accepted manner, as described by Schild for antagonists of biologically active compounds (*Brit. J. Pharmacol.* 2:189 (1947)) and expressed as pA$_2$ values (Table I).

Example XIV

Electrical Stimulation-GPI

The BKAn/mu-opioid receptor agonist heterodimers were evaluated for mu-opiate receptor activity in vitro using the electrically stimulated guinea pig ileum assay. This assay is well known in the art. The results are described in Table I. All heterodimers described in Table I comprise the BKAn peptide CP-0597 (unless otherwise indicated):

D-Arg-Arg-Pro-Hyp-Gly-Thi-Ser-D-Tic-NChg-Arg or a modified analog thereof, and is linked to the mu-opioid agonist via the linker moiety X represented by the group R1 or R2.

TABLE I

3-O-Alkylated Dihydromorphine Heterodimers:

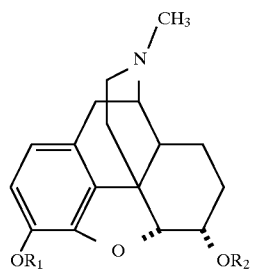

(all compounds are linked at the N-terminus of CP-0597 (unless otherwise indicated))

| CP# | R1 | R2 | mu-logIC$_{50}$ (GPI) | BK$_2$, pA$_2$ (GPA) |
|---|---|---|---|---|
| 695 | —(CH$_2$)$_{11}$—C(O)— | H | 5.9 | 8.3 |
| 699 | —(CH$_2$)$_5$—C(O)— | H | <5 | 8.5 |
| 756 | —(CH$_2$)$_{11}$—C(O)—NH—CH$_2$—(CH$_2$)$_4$—C(O)— | H | 5.28 | 8.4 |
| 834 | —(CH$_2$)$_8$—C(O)— | H | <5 | 8.2 |
| 844 | —(CH$_2$)$_{14}$—C(O)— | H | 5.6 | 7.5 |
| *697 | —(CH$_2$)$_{11}$—C(O)— | H | 6.3 | 8.3 |
| *700 | —(CH$_2$)$_5$—C(O)— | H | <5 | 8.1 |

3-O-Alkylated Morphine Heterodimer:

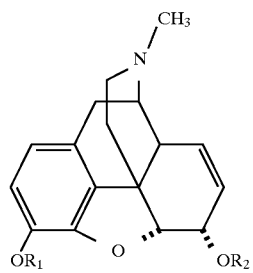

(all compounds are linked at the N-terminus of CP-0597)

| CP# | R1 | R2 | mu-logIC$_{50}$ (GPI) | BK$_2$, pA$_2$ (GPA) |
|---|---|---|---|---|
| 731 | —(CH$_2$)$_{11}$—C(O)— | H | 5.6 | 7.8 |

TABLE I-continued
| | | | | |
|---|---|---|---|---|
| 833 | 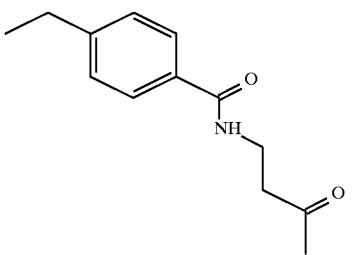 | H | <5 | 7.9 |
| 836 | 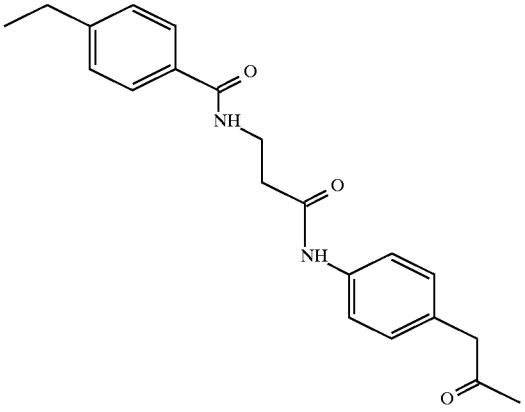 | H | <5 | 7.5 |
| 861 | 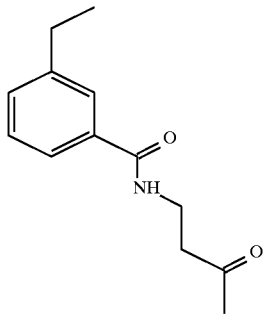 | H | <5 | 8.5 |
| 862 | 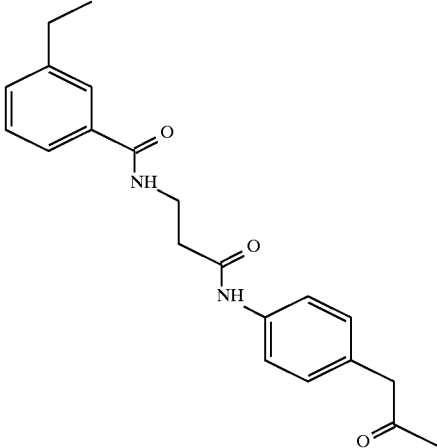 | H | <5 | 8.4 |

TABLE I-continued
6-O-Alkylated Dihydromorphine Heterodimers:
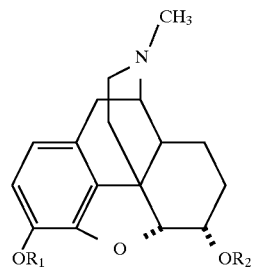
(all compounds are linked at the N-terminus of CP-0597)
| | | | | |
|---|---|---|---|---|
| 896 | H | —N(CH₂)₁₁—C(=O)— | 6.5 | 8.7 |
| 900 | H | —N(CH₂)₅—C(=O)— | 6.8 | 8.0 |
6-O-Alkylated Morphine Heterodimers:
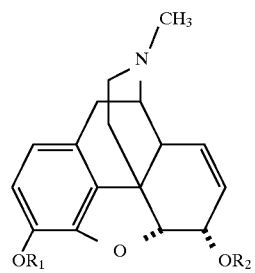
| | | | | |
|---|---|---|---|---|
| 902 | H | (butyl-phenyl-C(=O)CH₃, meta) | 6.2 | 8.7 |
| 903 | H | (ethyl-phenyl-C(=O)CH₃, meta) | 6.8 | 8 |
| 905 | H | (butyl-phenyl-C(=O)CH₃, para) | 6.7 | 7.9 |

TABLE I-continued

| 906 | H | 4-ethyl-acetophenone structure | 6.9 | 7.9 |

Anilino Subsituted Fentanyl Heterodimers:

[Structure: 4-anilino-1-phenethylpiperidine with R₁ on N and R₂ on piperidine C4]

(all compounds are linked at the N-terminus of CP-0597)

| 718 | hexane-2,5-dione | H | <5 | 8.5 |
| 719 | CH₃CO-CH₂-(CH₂)₅-CH₂-COCH₃ | H | 6.1 | 8.6 |
| 847 | hexane-2,5-dione | CH₂OCH₃ | 5.5 | 8.7 |
| 859 | CH₃CO-CH₂-(CH₂)₅-CH₂-COCH₃ | CH₂OCH₃ | 5.2 | 8 |

TABLE I-continued
C-3 Substituted Fentanyl Heterodimer:
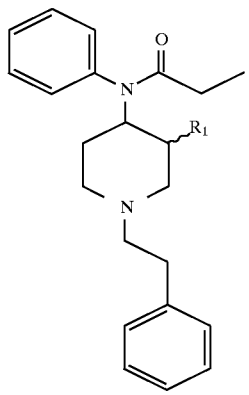
(all compounds are linked at the N-terminus of CP-0597)
| CP# | R1 | mu-logIC$_{50}$ (GPI) | BK$_2$, pA$_2$ (GPI) |
|---|---|---|---|
| 849 | (Isomer A) | 5.6 | 8.1 |
| 850 | (Isomers A & B) | 5.6 | 8.1 |
| 753 | (Isomer A) | 6.3 | 8.1 |
| 754 | (Isomer B) | 5.9 | 7.2 |
| 755 | (Isomers A & B) | 6.2 | 8.1 |
| 874 | (Isomers A & B) | 5.5 | 8.1 |
| 880 | (Isomer A) | 6.9 | 8.4 |

TABLE I-continued
| | | | |
|---|---|---|---|
| 881 | (Isomer B) | 5.6 | 7.8 |
C-4 Substituted Fentanyl Heterodimers:
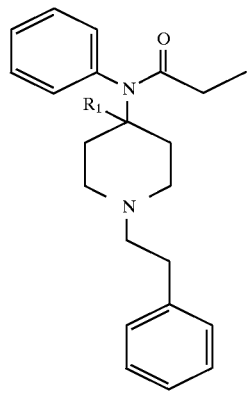
| | | | |
|---|---|---|---|
| 815 | | 5.9 | 6.6 |
| 823 | | 5.8 | 8.5 |
| 875 | | 5.8 | 7.3 |
| 884 | | 5.5 | — |
Phenyl Substituted Fentanyl Heterodimers:
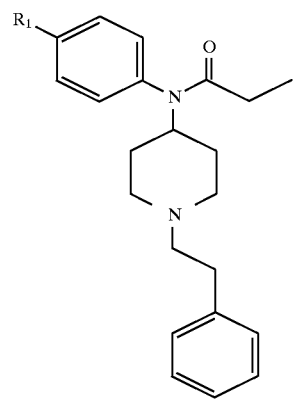

TABLE I-continued

| (all compounds are linked at the N-terminus of CP-0597) | | | |
|---|---|---|---|
| 872 | 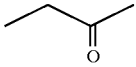 | <5 | 7.9 |
| 873 | 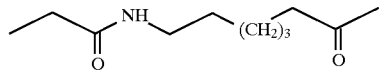 | <5 | 8.8 |
Lysine Scan Series Heterodimers with Substituted Fentanyl Analogues:
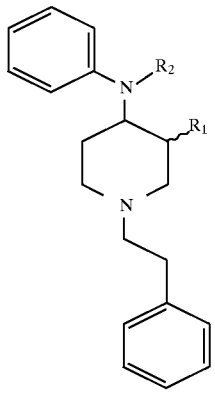
(Lysine was introduced in positions 0–1 of CP-0597 and linked to substituted fentanyl analogues:

| CP# | Lysine Postion within CP-0597 | R1 | R2 | mu-log$IC_{50}$ (GPI) | $BK_2$, $pA_2$ (GPI) |
|---|---|---|---|---|---|
| 727 | Lys(1) | H | 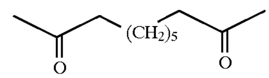  | 5.0 | 7.3 |
| 744 | Lys(1) |  (trans) | 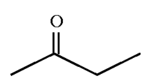  | 5.2 | 7.5 |
| 745 | Lys(1) |  (cis) | 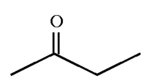  | 5.7 | 7.4 |
| 852 | DLys(0) |  (cis & trans) | 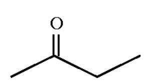  | 5.7 | 7.6 |
| 726 | Lys(1) | H | 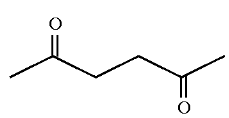  | 5.4 | 7.9 |

Lysine Scan Series Heterodimers with 3-O-Alkylated Dihydromorphine Analogues:

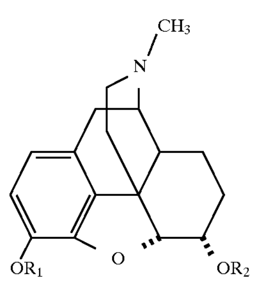

TABLE I-continued (Lysine was introduced in positions 0–6 of CP-0597 and linked at 3-0-Alkylated Dihydromorphine Analogues:)

| | | | | | |
|---|---|---|---|---|---|
| 840 | DLys(0) | 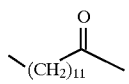 | H | 5.9 | 7.9 |
| 723 | Lys(1) | 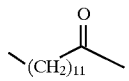 | H | 6.1 | 7.3 |
| 725 | Lys(1) | 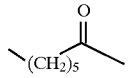 | H | <5 | 7.3 |
| 851 | Lys(2) | 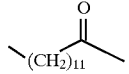 | H | 5.5 | 2.6 |
| 841 | Lys(3) | 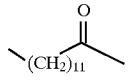 | H | 6.3 | <6 |
| 853 | Lys(4) | 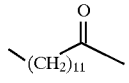 | H | 6.0 | <6 |
| 831 | Lys(5) | 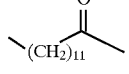 | H | 5.7 | 7.2 |
| 832 | Lys(6) | 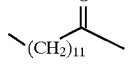 | H | 5.4 | 7.2 |
| 907 | DLys(0) | H | 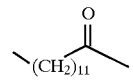 | 6.5 | — |

*= compounds linked at the N-terminus of B9340

Example XV

Isolation and Expression of the Human Mu Receptor Gene

A cDNA library from human brain (caudate /putamen) was obtained from Stratagene. The mu receptor sequence was selectively amplified from the cDNA library using nested PCR. The first round PCR used the two primers GTAAGAAACAGCAGGAGCTG (SEQ ID NO:1) and CAACCTGCTTCCACATACATG (SEQ ID NO:2) and Vent DNA polymerase (New England Biolabs). Twenty-four rounds of PCR were done using the following conditions: 94° C., 1 minute for denaturation, 60° C., 1 minute for annealing followed by 72° C., 3 minutes for extension. Excess primers were removed with a Centricon 30 miniconcentrator. A portion of this first round reaction was used as a template in a second round of PCR using the following primers GCGAAGCTTCAGTACCATGGACAGCA (SEQ ID NO:3) and CGCTCTAGAGGAATGGCATGAGACCC (SEQ ID NO:4). The number of rounds of PCR and the conditions were the same as those used for the first round. The DNA obtained after this second round was digested with the restriction enzymes Hind III and Xba I using standard methodology. Cesium chloride-purified pRc/CMV (Invitrogen) was also digested with Hind III and Xba I using standard methodology. The products of the two digests were resolved on a 0.7% low melt agarose gel. Sections of gel containing the human mu receptor DNA (approximately 1.2 kb) and the pRc/CMV DNA (approximately 5.5 kb) were excised from the gel. The gel slices containing these DNAs were heated at 65° C. and aliquots combined in a reaction containing T4 DNA ligase. The reaction was incubated overnight at 15° C. An aliquot of this reaction was used to transform frozen competent E. coli DH5α cells (GibcoBRL). Transformants containing the human mu receptor DNA were selected on LB+amp plates. One of the transformants was selected and the sequence of the human mu receptor DNA insert determined using the Sequenase enzyme (United States Biochemical) according to the manufacturer's instructions. This sequence was compared to the sequence of Wang et al. FEBS Letters 338:217 (1994)) as found in the Genbank database (accession number L25119). Three nucleotide missincorporations were detected and those that altered the amino acid sequence of the receptor were corrected using site-directed mutagenesis (Kunkel et al. Methods in Enzymology 154:367 (1987)). Cesium chloride-purified human mu receptor-pRc/CMV plasmid was transfected into CHO-K1 (ATCC) cells using the Lipofectamine reagent (GibcoBRL). Transfectants were selected with the antibiotic G418 and screened for $^3$H-DAMGO (Dupont NEN) binding. One clone, hmu5, was chosen based upon binding levels, binding kinetics and inhibition patterns as the clone to be used for all human mu receptor binding assays.

Example XVI

Human Mu Receptor Binding

Preparation of human MU clone membrane for binding assay was carried out by scraping cells from plate in ice cold PBS and centrifuging at 500×g, at 4° C. for 10 minutes. The supernatant was discarded and pellet resuspended in assay buffer consisting of 10 mM Tris/HCl, pH 7.4 with 0.32M Sucrose and centrifuged for 30 minutes, at 4° C., at 27,000× g. The supernatant was discarded and pellet resuspended in fresh assay buffer, and in 1 ml aliquots, frozen at −70° C. until needed.

Binding assays were performed by incubating human clone membrane solution (50 ug/well in 125 ul final concentration) with $^3$H-DAMGO (final concentration 5nM) with or without test compounds in assay buffer, at room temperature, for 60 minutes, at a final volume of 315 ul. All test compound dilutions were done in triplicate. Assays were harvested by quick filtration in a Tomtec Harvester 96, with ice-cold wash buffer consisting of 50 mM Tris/HCl, pH 7.4, onto Wallec printed glassfiber Filtermat "B", which had been pre-soaked with 0.1% PEI and previously air-dried. Filtermats were counted in 9.5 mls Wallec Beta-Plate Scint, in Wallec 1450 MicroBeta Counter. Data is shown in Table II.

Example XVII

BK Human Receptor Cloning

RNA was isolated from human lung fibroblasts (CCD-16 LU obtained from the ATCC) using the method of Ghirgwin et al (*Biochemistry* 18:5294 (1979)). The RNA was transcribed into cDNA using MMlV reverse transcriptase, the primer GACTCGAGTCGACATC-GATTTTTTTTTTTTTTTTT (SEQ ID NO:5) and the procedure of Maniatis (*Molecular Cloning* Cold Spring Harbor Laboratory (1982)). The human BK2 receptor cDNA was selectively amplified using nested PCR. The first round PCR used the two primers CTCCGAGGAGGGGTGGG (SEQ ID NO:6) and CCTGAAAAGCAACTGTCCC (SEQ ID NO:7) and Taq DNA polymerase (Promega). Twenty-five rounds of PCR were done using the following conditions: 94° C., 1 minute for denaturation, 50° C., 1 minute for annealing followed by 72° C., 3 minutes for extension. Excess primers were removed with a Centricon 30 miniconcentrator. A portion of this first round reaction was used as a template in a second round of PCR using the following primers GCGAAGCTTCGTGAGGACTCCGTGCCC (SEQ ID NO:8) and CGCTCTAGACAAATTCACAGCCC (SEQ ID NO:9). The number of rounds of PCR and the conditions were the same as those used for the first round. The DNA obtained after this second round was digested with the restriction enzymes Hind III and Xba I using standard methodology. Cesium chloride-purified pRc/CMV (Invitrogen) was also digested with Hind III and Xba I using standard methodology. The products of the two digests were resolved on a 1% low melt agarose gel. The human BK2 receptor DNA (approximately 1.1 kb) and the pRc/CMV DNA (approximately 5.5 kb) were excised from the gel. The gel slices containing these DNAs were heated at 65° C. and aliquots combined in a reaction containing T4 DNA ligase. The reaction was incubated overnight at 15° C. An aliquot of this reaction was used to transform frozen competent *E. coli* DH5α cells (Gibco/BRL). Transformants containing the human BK2 receptor DNA were selected on LB+amp plates. One of the transformants was selected and the sequence of the human BK2 receptor DNA insert determined using the Sequenase enzyme (United States Biochemical) according to the manufacturer's instructions. This sequence was compared to the sequence of Hess et al (*Biochemical and Biophysical Research Communications* 184:260 (1992)). Two nucleotide missincorporations were detected and those that altered the amino acid sequence of the receptor were corrected using side-directed mutagenesis (Kunkel et al., *Methods in Enzymology* 154:367 (1987)). The human BK2 receptor-pRc/CMV plasmid was transfected into CHO-K1 (ATCC) cells using the Lipofectamine reagent (Gibco/BRL). Transfectants were selected with antibiotic G418 and screened for $^3$H-bradykinin (Dupont NEN) binding. One clone, S34f, was chosen based upon binding levels, binding kinetics and inhibition patterns as the clone to be used for all human BK2 receptor binding assays.

Example XVIII

Human BK2 Receptor Binding

Preparation of human BK2 clone membrane for binding assay was carried out by scraping cells from roller bottles in ice cold PBS and centrifuging at 1000×g, at 4° C. for 15 minutes. The supernatant was discarded and pellet resuspended in Buffer A consisting of 25 mM TES(pH 6.8) with 2 uM 1,10-Phenanthroline, and centrifuged at 27,000×g for 15 min. this was then repeated. The final pellet was resuspended in Buffer B (Buffer A with 2 uM Captopril, 140 ug/Ml Bacitracin, 0.1% BSA), and stored in 1 ml aliquots, frozen at −20° C. until needed.

Binding assays were performed by incubating human clone membrane solution (Approx. 60 ug/well in 125 ul) with $^3$H-Bradykinin (final concentration 0.3 nM) with or without test compounds in assay buffer B with 1 mM Dithiotreitol), at room temperature, for 45 minutes, at a final volume of 315 ul. All test compound dilutions were done in triplicate. Assays were harvested by quick filtration in a Tomtec Harvester 96, with ice-cold wash buffer consisting of 10 mM Tris/HCl, pH 7.5, 100 mM NaCl,0.02% BSA, onto Wallec printed glassfiber Filtermat "B", which had been pre-soaked with 0.1% PEI and previously air-dried. Filtermats were counted in 9.5 mls Wallec Beta-Plate Scint, in Wallec 1450 MicroBeta Counter. Data is shown in Table II.

TABLE II

| BK/Mu Heterodimer # | Mu Binding Human Clone | BK-2 Binding Human Clone $pIC_{50}$ |
|---|---|---|
| 695 | NT | 8.9 |
| 719 | 6.4 | 8.9 |
| 723 | 7.6 | 9.4 |
| 725 | 6.1 | NT |
| 726 | 6.3 | NT |
| 744 | 6.4 | NT |
| 745 | 6.8 | NT |
| 754 | <5 | NT |
| 755 | 7.8 | NT |
| 756 | 7.9 | NT |
| 815 | 7.5 | NT |
| 823 | 7 | NT |
| 831 | NT | 6.9 |
| 832 | 7.6 | NT |
| 836 | 6.1 | 8.9 |
| 840 | 7.95 | 8.9 |
| 841 | 7.9 | 7.9 |
| 844 | NT | 8.5 |
| 847 | NT | 9.6 |
| 849 | NT | 9.2 |
| 850 | NT | 9.2 |
| 851 | 8.1 | 7.4 |
| 852 | 7.4 | 9 |
| 853 | 7.8 | 7.2 |
| 859 | 6.8 | 8.5 |
| 861 | 6.1 | NT |

TABLE II-continued

| BK/Mu Heterodimer # | Mu Binding Human Clone | BK-2 Binding Human Clone pIC$_{50}$ |
|---|---|---|
| 862 | 6.3 | 9 |
| 865 | 7.2 | 6.3 |
| 872 | 5.8 | NT |
| 873 | 5.4 | NT |
| 874 | NT | 8.3 |
| 875 | 7.6 | 8.7 |
| 877 | 7.2 | 7.9 |
| 880 | 8.1 | 8.8 |
| 881 | 7.4 | 8.7 |
| 884 | 7.3 | 8.7 |
| 889 | 7.1 | 7.8 |
| 890 | 7.2 | 6.9 |
| 896 | 8.3 | 8.7 |
| 900 | 8.6 | 8.8 |
| 902 | 8.4 | 9.4 |
| 903 | 8.8 | 9.3 |
| 905 | 8.3 | 9.3 |
| 906 | 8.3 | 9.3 |
| 907 | 8.2 | 9.0 |
| 910 | 8.6 | NT |
| 911 | 8.5 | NT |
| 912 | 5.2 | NT |
| 913 | 5.4 | NT |

NT = not tested

In Vivo Studies

The effect of dihydromorhine and the heterodimer CP-0840 are described below, but essentially similar results were observed with fentanyl and its heterodimer, CP-0719.

Example XIX

Mouse Formalin Test

This test is a classical test for opiate and non-steroidal analgesic compounds. Mice are pretreated s.c. with vehicle or compound 30 minutes before injecting the formalin. 10 μl of 5% formalin was injected into one paw of a mouse. This resulted in a characteristic behavioral response reflective of pain, characterized by licking the paw. The time spent licking the paw from 0–5 min (early phase response) and 15–30 min (late phase response) was measured.

Figure 2:
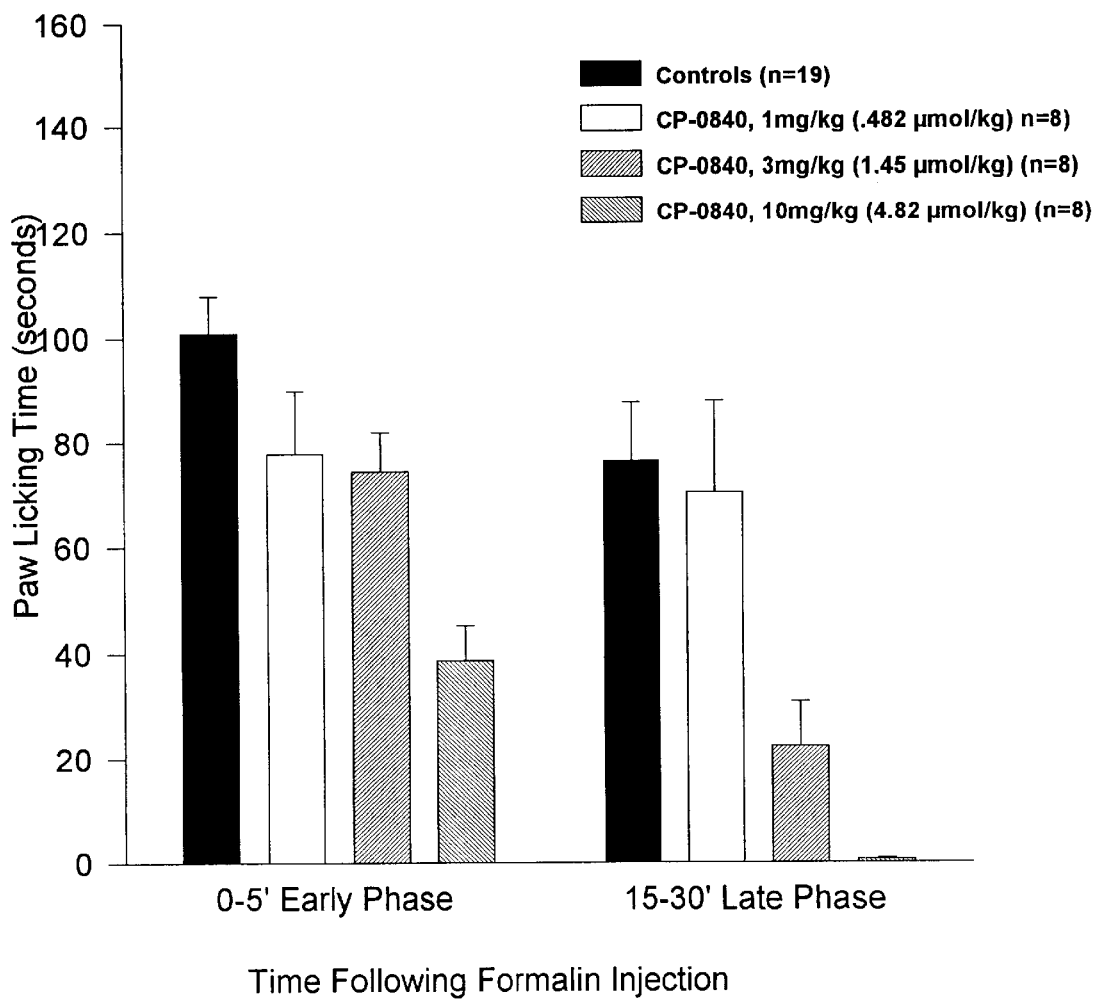
FIG. 2 shows the effect of CP-0840 on paw licking time following 10 $\mu$l formalin injection.

FIGS. 1 and 2 show the effect of dihydromorphine and the heterodimer, CP-0840, both of which produced a dose-dependent inhibition of the first and second phase responses compared to vehicle control animals. The mean ED$_{50}$'s (dose in μmole/kg producing a 50% reduction of the first and second phase response) for dihydromorhine in the first and second phase were 6.7 and 4.3, whereas those for CP-0840 were 3.2 and 1.0, respectively. This reflects an increase in potency for CP-0840 compared to dihyromorphine. It is to be noted in this test that CP-0597 (the BK antagonist) had no significant effect on either phase at doses ranging from 0.3–10 mg/kg s.c.

It was noticed that in all mice given dihydromorhine a typical Straub tail effect (erection and bending of the tail over the back of the animal) was observed, an effect not seen with any of the doses of CP-0840. This suggests that CP-0840 does not get into the CNS since it is known that the Straub tail phenomenon is centrally mediated.

Example XX

Mouse Hot Plate

This is another classic test for analgesics whose mechanism of action involves spinal (central nervous system) pathways. Essentially, mice were placed on a surface maintained at 55° C. and the time taken for the animal to respond by raising one of the hind paws was recorded. Vehicle or test compound were given and the mouse placed on the hot plate. Reaction time was recorded at time intervals up to 240 minutes.

Figure 3:
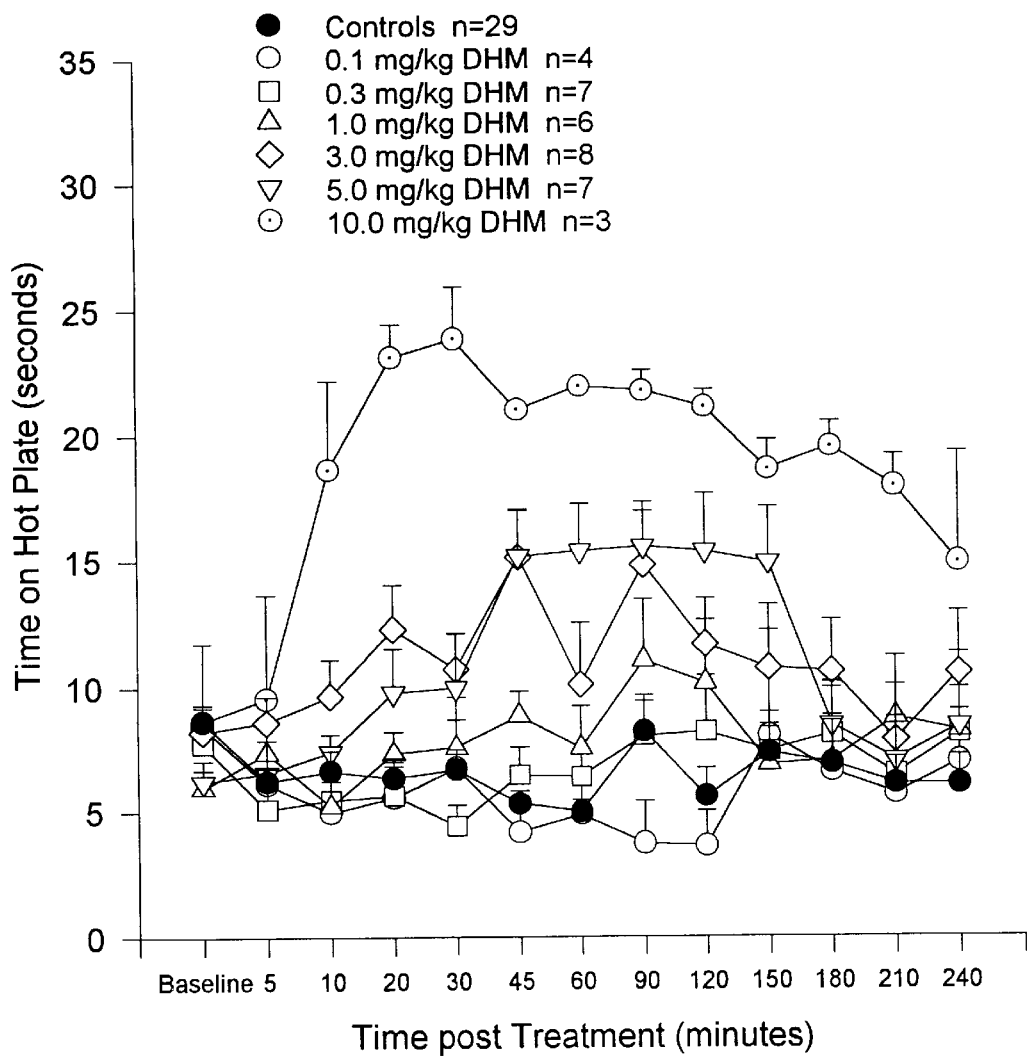
FIG. 3 shows the effect of dihydormorphine on the response time of mice exposed to a hot surface.
Figure 4:
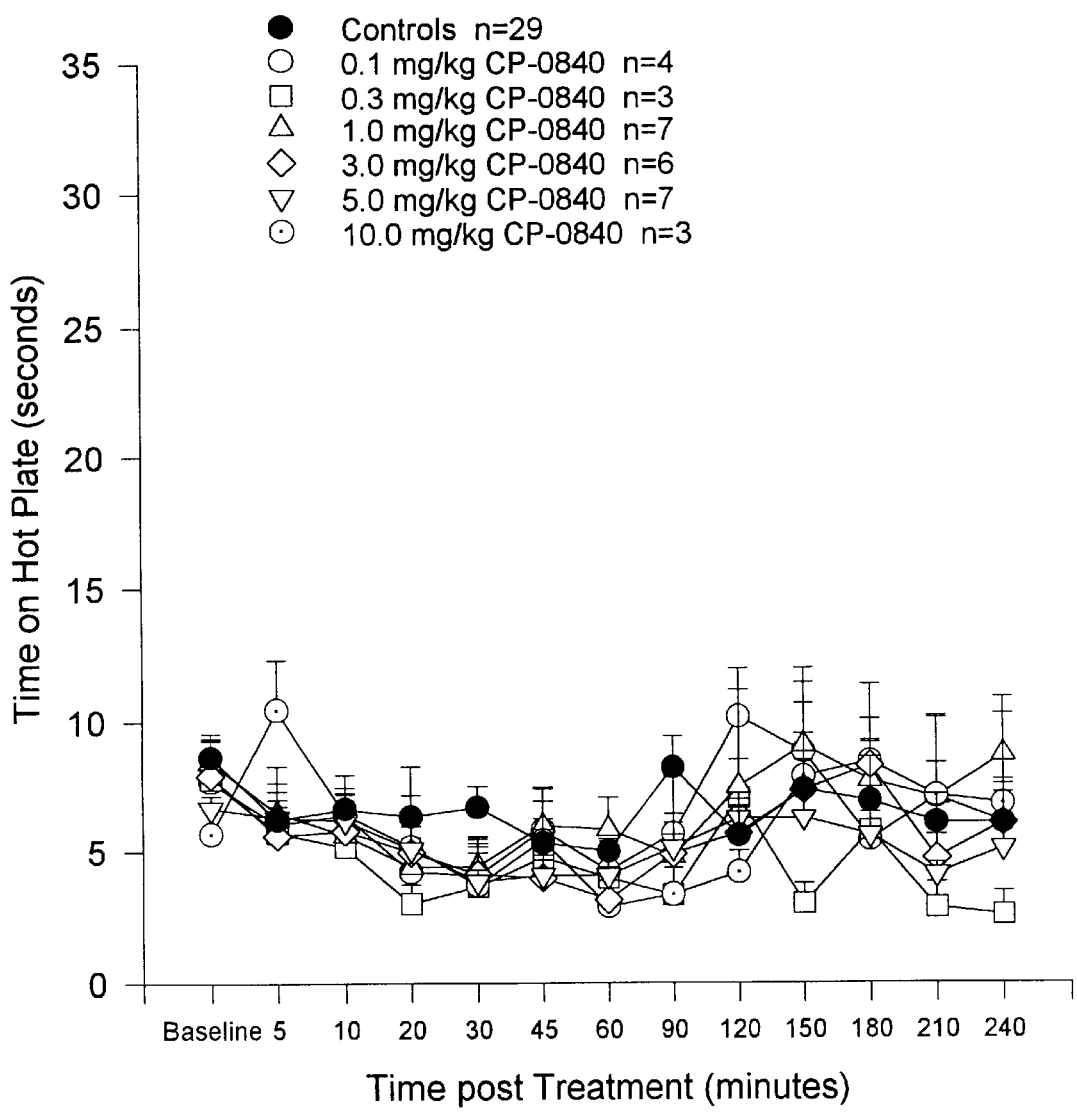
FIG. 4 show s the effect of CP-0840 on the response time of mice exposed to a hot surface.

Dihydromorhine produced a dose dependent increase in the time spent on the hot plate (FIG. 3), whereas CP-0840 had no effect compared to vehicle controls at all doses studied (FIG. 4).

Example XXI

Rat Carrageenan Paw Edema

This test is designed to assess the anti-inflammatory effects of compounds as reflected by the edema component of the response. The volume of the paw was measured before and after injection of carragenan at 1 h intervals over a 6 h time period using a Ugo Basile Plesthysmometer. Vehicle or test compounds were injected s.c. 30 min before injecting the carrageenan. Carrageenan (1%) was injected subplantar into one paw of a rat.

Figure 5:
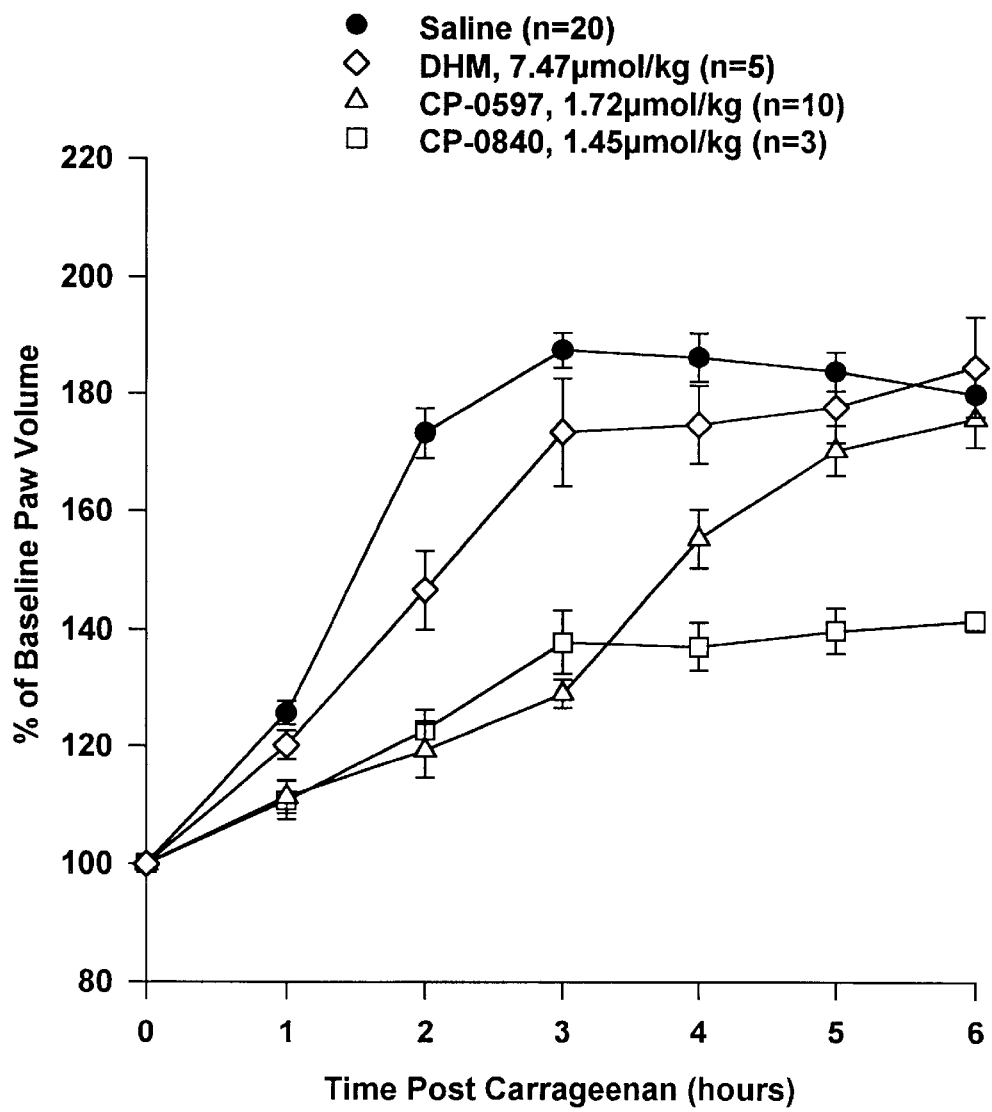
FIG. 5 compares the effect of saline, DHM, CP-0597 and CP-0840 on carrageenan (1% i.pl.) induced edema in the rat hind paw.
Figure 6:
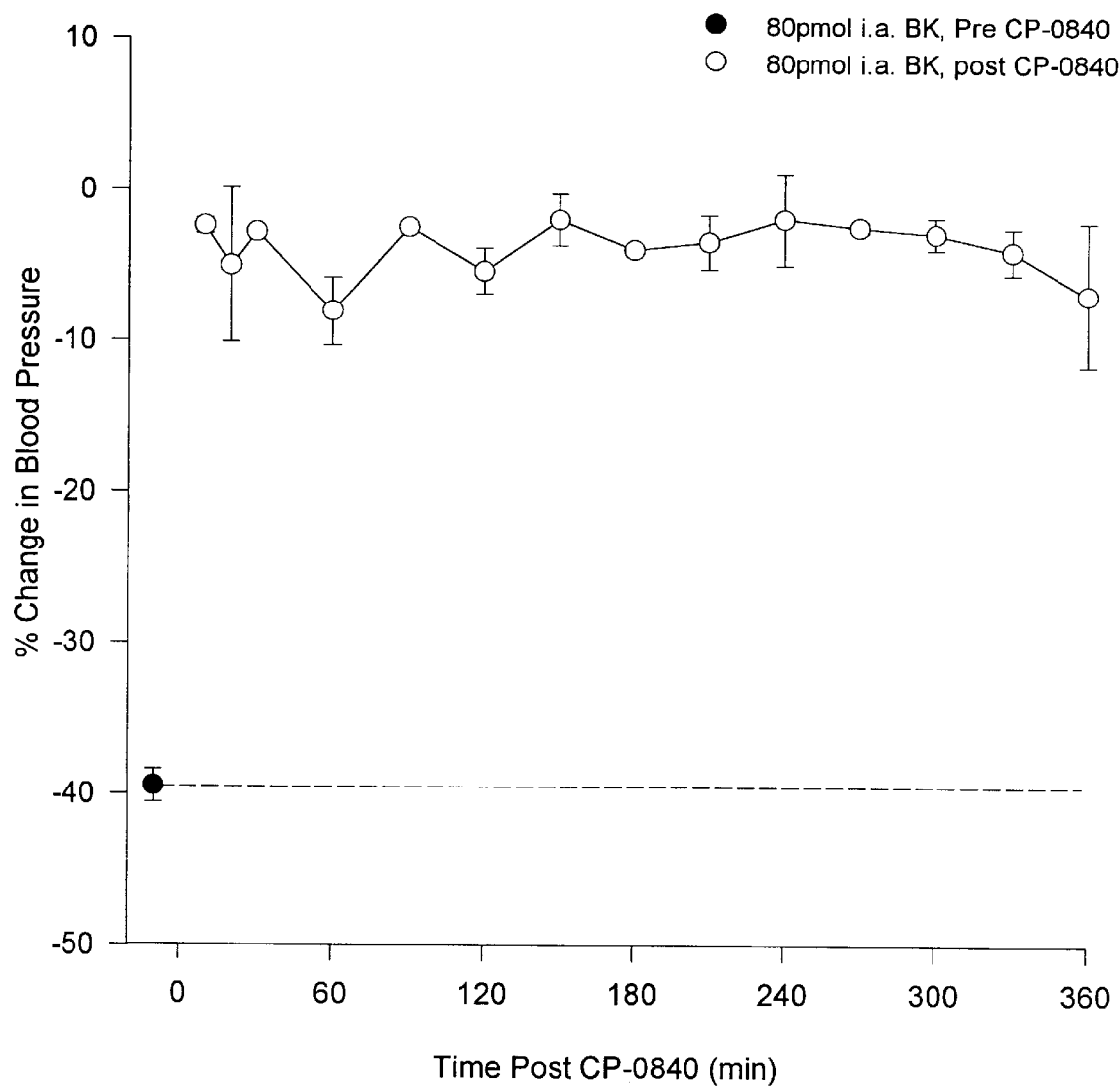
FIG. 6 shows the duration of action of CP-0840 in rats.

FIG. 5 compares the effect of pretreatment of the rats with saline, dihydromorhine, CP-0597 (BK antagonist) and the heterodimer, CP-0840. It can be seen that dihydromorhine had little to no effect on the edema response. CP-0597, the BK antagonist, produced significant inhibition from 0–3 h, however, the edema response recovered at time 5–6 h. In contrast, the heterodimer, CP-0840 produced significant inhibition of the edema response at all time points. Careful analysis of the responses revealed a 2 phase response to carrageenan; an early ,0–3 h, and a late, 3–6 h phase. The percentage inhibition of the edema response at times 3 and 6 h for each compound are shown in Table 3. The heterodimer was clearly effective over the whole 6 h in contrast to the individual components. CP-0840 (as does CP-0597) at this dose had a duration of action of greater than 6 h in the rat against blood pressure responses to bradykinin (FIG. 6). Therefore, the lack of effect of CP-0597 from time 4–6 cannot be attributable to its disappearance from the receptors. CP-0840 is showing a clear co-operativity phenomenon possibly reflecting an opiate sensitive component during the second phase.

Table 3. Percentage inhibition of the carrageenan paw edema produced by dihydromorphine (DHM), the BK antagonist CP-0597 and the heterodimer CP-0840 at time 3 and 6 h post carrageenan compared to saline controls.

|  | DHM | CP-0597 | CP-0840 |
|---|---|---|---|
| 3 h | 0 | 66.3 | 56.6 |
| 6 h | 0 | 0 | 45.9 |

Example XXII

Mustard Oil-induced neurogenic inflammation in the Rat

Figure 7:
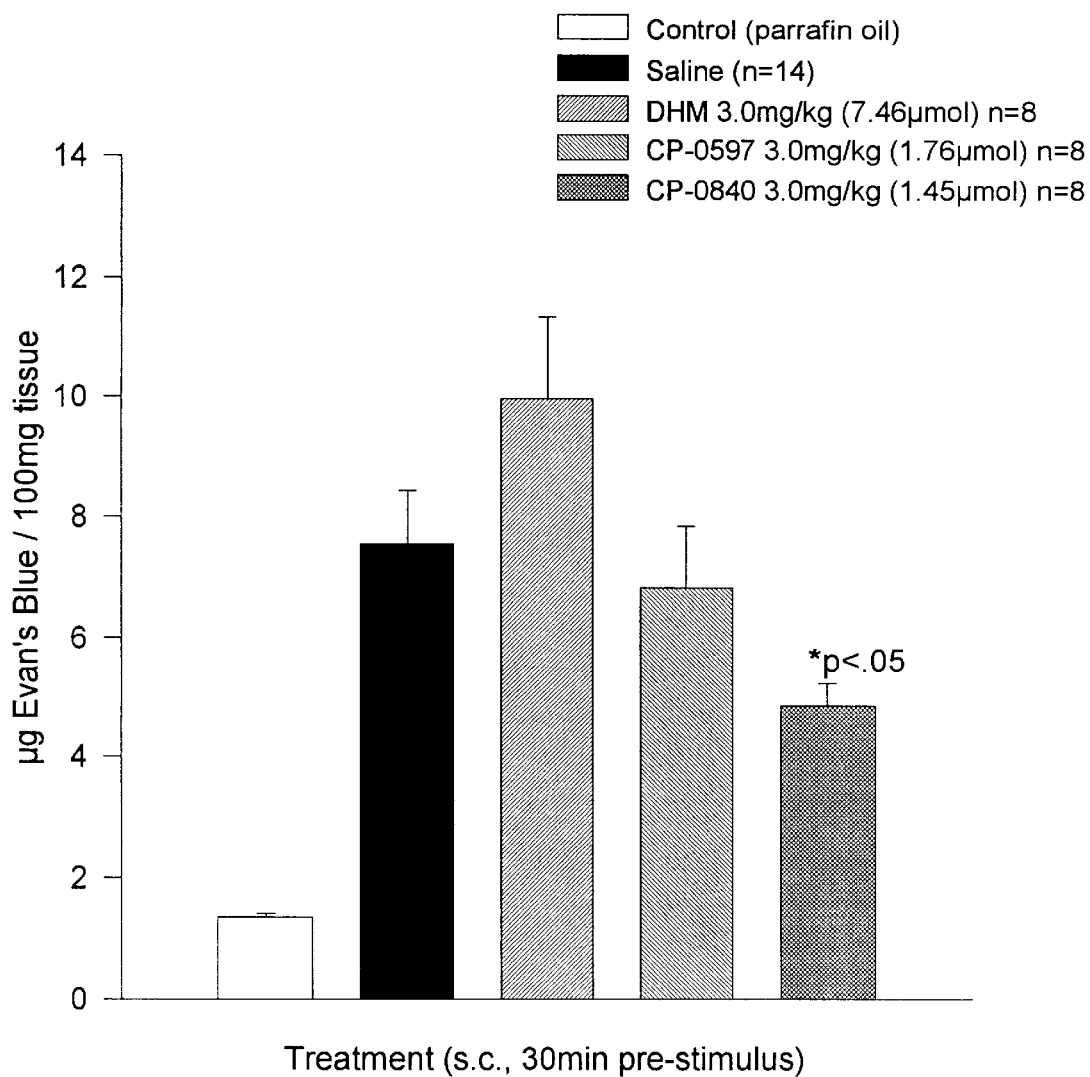
FIG. 7 compares the effect of saline, DHM, CP-0597 and CP-0840 on mustard oil induced neurogenic inflammation in the rat hind paw.

Mustard oil was applied to the skin of the rat hind paw. This causes activation of nerve terminals in the skin which release neuropeptides which produce vasodilation and an increase in permeability of the microvasculature resulting in an increase in paw edema. Evan's blue dye was injected i.v. at a dose of 30 mg/kg. The animal was sacrificed 15 minutes after applying the mustard oil and the skin from the paw was removed and placed in formamide for 48 h. The amount of Evan's blue dye as ug/100 mg tissue was calculated spectroflourometrically at 620 nM from a standard curve. FIG. 7 compares the effect of dihydromorphine, CP-0597 and CP-0840 in this model. At the doses used CP-0840 produced a significant inhibition of the edema response compared to saline controls. Dihydromorphine and CP-0597 at the doses used were without effect.

Example XXIII

Rat Blood Pressure

Figure 8:
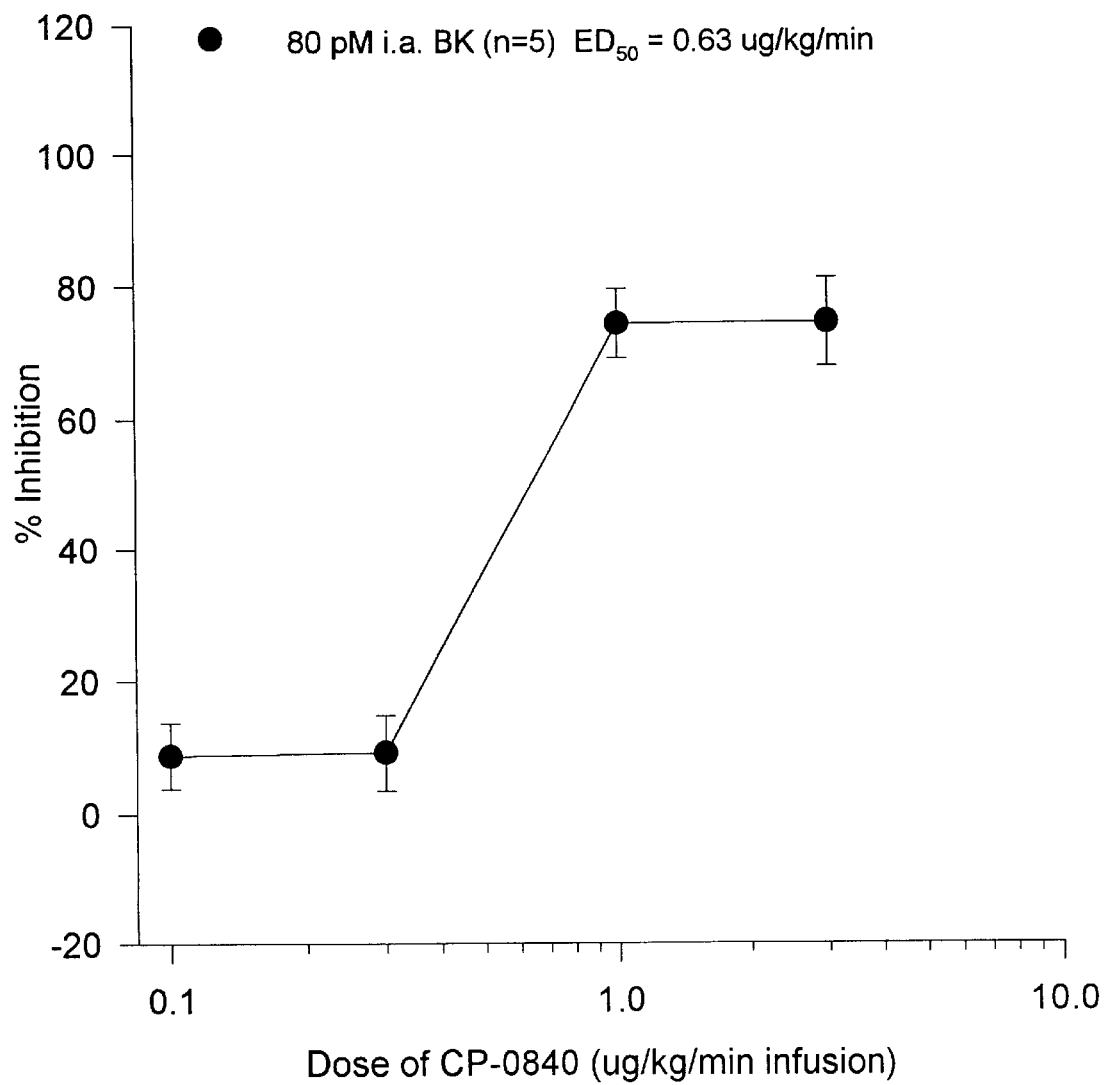
FIG. 8 shows the effect of CP-0840 on the hypotensive response to bradykinin.
Figure 9:
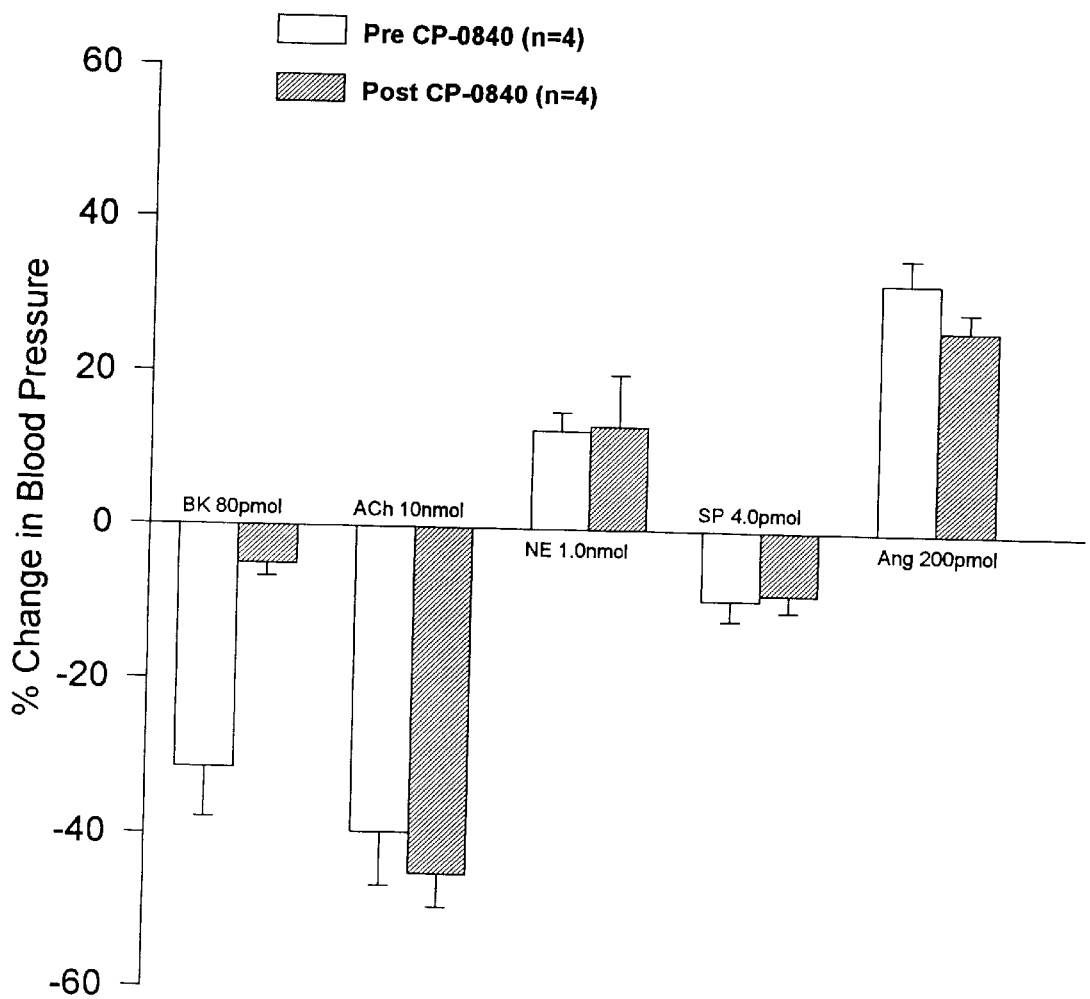
FIG. 9 shows the selectivity of CP-0840.

Male rats were anesthetised with urethane, 1.25 g/kg, and cannulae were placed in the carotid artery and femoral vein for the injection and infusion of compounds and in the femoral artery for the recording of blood pressure. Standard hypotensive responses were obtained to repeated administration of bradykinin, 80 pM. These were repeated in the presence of increasing dose infusions of CP-0840. The dose of CP-0840 reducing the hypotensive response to bradykinin by 50% (ED50) was calculated and found to be 0.63 ug/kg/min (FIG. 8). The selectivity of CP-0840 was assessed at a dose of 3 ug/kg/min. At this dose hypotensive responses to bradykinin (80 pM) were completely blocked but not those to acetylcholine (10 nM) or substance P (4 pM), nor were the hypertensive responses to norepinephrine (1 nM) or angiotensin (200 pM). CP-0840 can be said to be a selective antagonist of bradykinin in vivo in the rat blood pressure assay (FIG. 9).

We claim:
1. A heterodimer of the formula:

(BKAn)(X)(Y)

where BKAn is a bradykinin antagonist peptide selected from:

DArg$^0$-Arg$^1$-Pro$^2$-Hyp$^3$-Gly$^4$-Iglb$^5$-Ser$^6$-DIglb$^7$-Oic$^8$-Arg$^9$;

DArg$^0$-Arg$^1$-Pro$^2$-Hyp$^3$-Gly$^4$-Thi$^5$-Ser$^6$-DIglb$^7$-Oic$^8$-Arg$^9$;

DArg$^0$-Arg$^1$-Pro$^2$-Hyp$^3$-Gly$^4$-Iglb$^5$-Ser$^6$-D-Tic$^7$-NChg$^8$-Arg$^9$;

or an analog thereof, said analog comprising an L-Arg or L-Lys in the 0-position or a D- or L-Lys in the 0–6 position of said peptide;

Y is dihydromorphine or morphine; and

X is a linker;

where X is attached to said BKAn peptide via the 0, 1, 2, 3, 5 or 6 position amino acid residue of said peptide;

wherein said heterodimer retains bradykinin antagonist activity.

2. The heterodimer according to claim 1 wherein Y is

[structure of dihydromorphine derivative with OR$_1$ and OR$_2$]

or

[structure of morphine derivative with OR$_1$ and OR$_2$]

and R1 and R2 are independently selected from

[structures: -(CH$_2$)n-C(O)- where n = 1 to 20; -(CH$_2$)n-C(O)-NH-CH$_2$-C(O)- where n = 1 to 15; benzene ring with R3 and R4 substituents (meta or para)]

where R3 is (CH$_2$)n where n=1 to 4 and R4 is C(O); CH$_2$C(O); CONH(CH$_2$)$_2$C(O) or CONH(CH$_2$)$_2$CONH(Phe) CH$_2$C(O); or R1 or R2 is H;

provided that either R1 or R2 is the linker group X.

3. The heterodimer according to claim 2 wherein Y is

[structure of morphine derivative with OR$_1$ and OR$_2$]

and R1 is

[structure: -(CH$_2$)$_{11}$-C(O)-]

and R2 is H.

4. The heterodimer according to claim 3 wherein BKAn is

DLys-Arg-Pro-Hyp-Gly-Thi-Ser-D-Tic-NChg-Arg.

5. The heterodimer according to claim 2 wherein Y is

[structure of morphine derivative with OR$_1$ and OR$_2$]

and R1 is H and R2 is

[structure: ethyl-substituted benzene ring with C(O)]

6. The heterodimer according to claim 5 wherein BKAn is

DArg-Arg-Pro-Hyp-Gly-Thi-Ser-D-Tic-NChg-Arg.

7. A heterodimer of the formula:

(BKAn)(X)(Y)

where BKAn is a bradykinin antagonist peptide;

Y is fentanyl; and

X is a linker;

where X is attached to said BKAn peptide via the 0, 1, 2, 3, 5 or 6 position amino acid residue of said peptide;

wherein said heterodimer retains bradykinin antagonist activity.

8. The heterodimer according to claim 7 wherein Y is

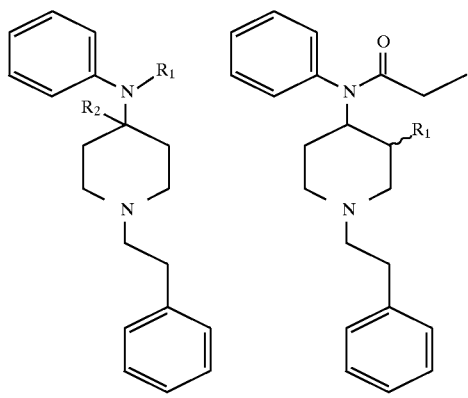

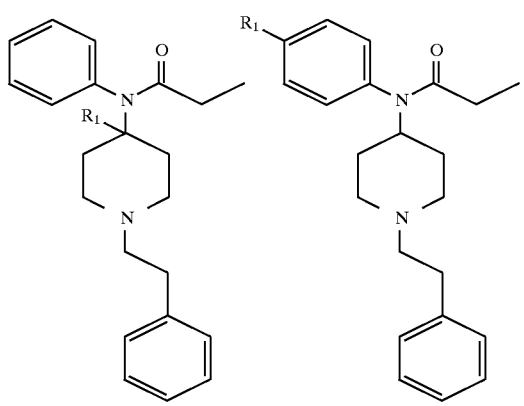

or

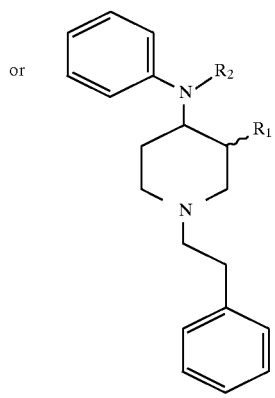

and R1 and R2 are independently selected from

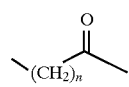 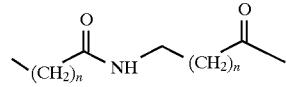

where n = 1 to 20    where n = 1 to 15

-continued

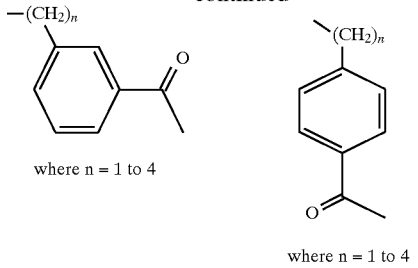

where n = 1 to 4 where n = 1 to 4

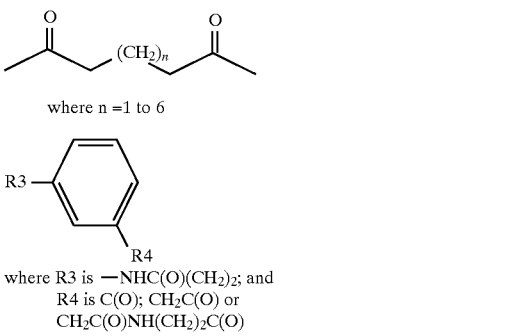

where n = 1 to 6 where R3 is —NHC(O)(CH$_2$)$_2$; and
R4 is C(O); CH$_2$C(O) or
CH$_2$C(O)NH(CH$_2$)$_2$C(O)

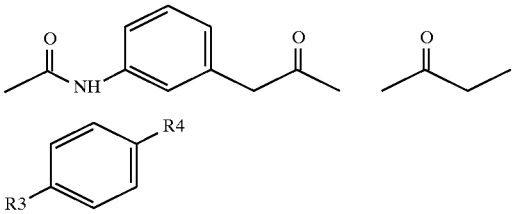

where R3 is CO(CH$_2$)$_2$NH— and
R4 is —CONH(CH$_2$)$_2$CO where R3 is (CH$_2$)$_4$NHCO— and
R4 is —CONH(CH$_2$)$_2$CO or H;

provided that either R1 or R2 is the linker group X.

9. The heterodimer according to claim 8 wherein Y is

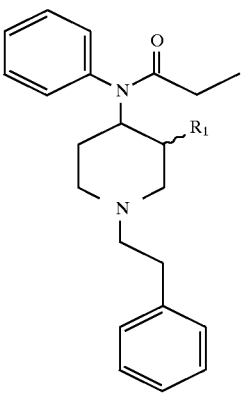

and R1 is the A isomer of

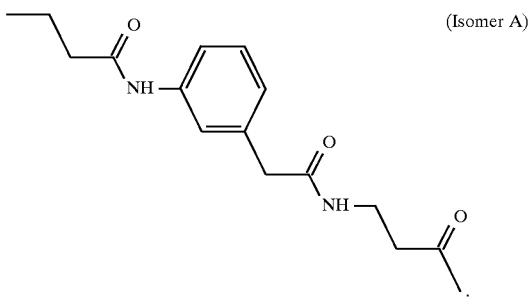

(Isomer A)

10. The heterodimer according to claim 9 wherein BKAn is
   D-Arg-Arg-Pro-Hyp-Gly-Thi-Ser-D-Tic-NChg-Arg.
11. The heterodimer according to claim 8 wherein Y is

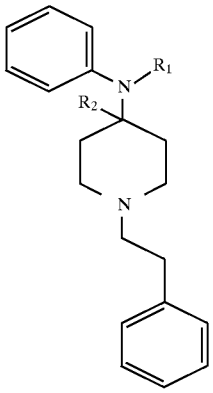

and R1 is

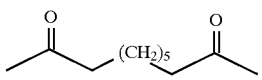

and R2 is H.

12. The heterodimer according to claim 11 wherein BKAn is
   D-Arg-Arg-Pro-Hyp-Gly-Thi-Ser-D-Tic-NChg-Arg.
13. The heterodimer according to claim 7 wherein Y is

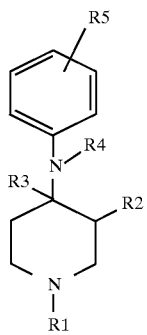

where
   R1 is a linking group X of the formula CH₂CH₂(Phe) CH₂C(O);
   R2, R3, R5 are H; and
   R4 is COCH₂CH₃.
14. The heterodimer according to claim 7 wherein BKAn is D-Arg-Arg-Pro-Hyp-Gly-Iglb-Ser-DIglb-Iglb-Arg;
D-Arg-Arg-Pro-Hyp-Gly-Iglb-Ser-DIglb-Oic-Arg;
D-Arg-Arg-Pro-Hyp-Gly-Thi-Ser-DIglb-Oic-Arg;
D-Arg-Arg-Pro-Hyp-Gly-Thi-Ser-D-Tic-NChg-Arg;
D-Arg-Arg-Pro-Hyp-Gly-Phe-Ser-D-Tic-NChg-Arg;
D-Arg-Arg-Pro-Hyp-Gly-Thi-Ser-D-Tic-Oic-Arg; or
D-Arg-Arg-Pro-Hyp-Gly-Phe-Ser-DHypTE-Oic-Arg.

15. The heterodimer according to claim 14 wherein the amino residue in the 0 to 6 position of the BKAn is substituted with D- or L-Lys.
16. The heterodimer according to claim 14 wherein the D-Arg in the "0" position is substituted with L-Arg or L-Lys.
17. A pharmaceutical composition comprising a heterodimer according to claim 1 or 7 and a pharmaceutically acceptable carrier.
18. A method of treating pain or inflammation in a host in need of such treatment comprising adminstering an effective amount of a heterodimer according to claim 1 or 7.
19. The heterodimer of claim 7 wherein Y is

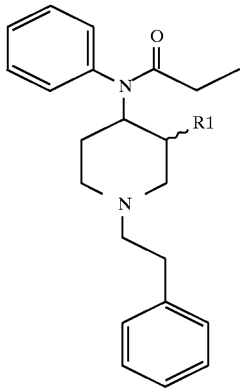

and R1 is

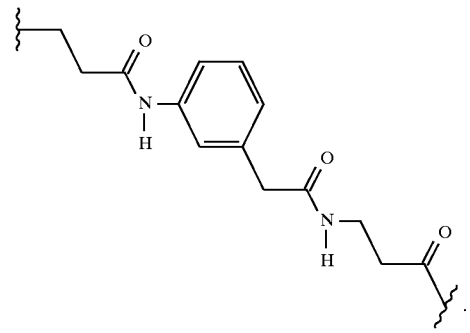

20. The heterodimer of claim 19 wherein BKAn is
   α-Lys-Arg-Pro-Hyp-Gly-Thi-Ser-D-Tic-NChg-Arg;
   D-Arg-Arg-Pro-Hyp-Gly-Phe-Ser-D-Tic-NChg-Arg;
   α-Lys-Arg-Pro-Hyp-Gly-Phe-Ser-D-Tic-NChg-Arg;
   ε-Lys-Arg-Pro-Hyp-Gly-Thi-Ser-D-Tic-NChg-Arg; or
   ε-Lys-Arg-Pro-Hyp-Gly-Phe-Ser-D-Tic-NChg-Arg.
21. The heterodimer of claim 19 wherein BKAn is
   L-Arg-Arg-Pro-Hyp-Gly-Thi-Ser-D-Tic-NChg-Arg; or
   L-Arg-Arg-Pro-Hyp-Gly-Phe-Ser-D-Tic-NChg-Arg.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

GTAAGAAACA GCAGGAGCTG 20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CAACCTGCTT CCACATACAT G 21

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GCGAAGCTTC AGTACCATGG ACAGCA 26

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CGCTCTAGAG GAATGGCATG AGACCC 26

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GACTCGAGTC GACATCGATT TTTTTTTTT TTTTT 35

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTCCGAGGAG GGGTGGG 17

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CCTGAAAAGC AACTGTCCC 19

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GCGAAGCTTC GTGAGGACTC CGTGCCC 27

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CGCTCTAGAC AAATTCACAG CCC 23